(12) United States Patent
Guire et al.

(10) Patent No.: US 7,772,393 B2
(45) Date of Patent: Aug. 10, 2010

(54) PHOTOCHEMICAL CROSSLINKERS FOR POLYMER COATINGS AND SUBSTRATE TIE-LAYER

(75) Inventors: Patrick Guire, Eden Prairie, MN (US); Kristin Taton, Little Canada, MN (US); Jie Wen, Eden Prairie, MN (US)

(73) Assignee: Innovative Surface Technologies, Inc., St. Paul, MN (US)

( * ) Notice: Subject to any disclaimer, the term of this patent is extended or adjusted under 35 U.S.C. 154(b) by 921 days.

(21) Appl. No.: 11/423,503

(22) Filed: Jun. 12, 2006

(65) Prior Publication Data

US 2007/0003707 A1    Jan. 4, 2007

Related U.S. Application Data

(60) Provisional application No. 60/690,018, filed on Jun. 13, 2005, provisional application No. 60/709,330, filed on Aug. 18, 2005, provisional application No. 60/804,222, filed on Jun. 8, 2006.

(51) Int. Cl.
  C07D 251/32    (2006.01)
  C07D 251/34    (2006.01)
  C08K 5/3492    (2006.01)
  C09K 11/06    (2006.01)

(52) U.S. Cl. .................. 544/196; 544/221; 252/301.23; 524/100; 524/101

(58) Field of Classification Search ................. 544/221, 544/196; 252/301.23, 301, 23; 524/100, 524/101
See application file for complete search history.

(56) References Cited

U.S. PATENT DOCUMENTS

| | | | |
|---|---|---|---|
| 3,959,078 A | 5/1976 | Guire | |
| 4,605,413 A | 8/1986 | Urry et al. | |
| 4,722,906 A | 2/1988 | Guire | |
| 5,002,582 A | 3/1991 | Guire et al. | |
| 5,331,027 A | 7/1994 | Whitbourne | |
| 5,414,075 A | 5/1995 | Swan et al. | |
| 5,637,460 A | 6/1997 | Swan et al. | |
| 5,714,360 A | 2/1998 | Swan et al. | |
| 5,942,555 A | 8/1999 | Swanson et al. | |
| 6,077,698 A | 6/2000 | Swan et al. | |
| 6,096,369 A | 8/2000 | Anders et al. | |
| 6,278,018 B1 | 8/2001 | Swan | |
| 6,391,948 B1 * | 5/2002 | Clark et al. | 524/101 |
| 7,348,055 B2 | 3/2008 | Chappa et al. | |
| 2008/0021126 A1 * | 1/2008 | Dietliker et al. | 522/34 |

FOREIGN PATENT DOCUMENTS

| | | |
|---|---|---|
| WO | WO 93/16176 | 8/1993 |
| WO | WO 97/07161 | 2/1997 |
| WO | WO 03/097117 A1 | 11/2003 |

OTHER PUBLICATIONS

Kroschwitz, ed. "Plastics", Concise Encyclopedia of Polymer Science and Engineering, John Wiley & Sons, 1990, pp. 462-464.
International Search Report (pp. 1-4).
Allen, et al., "Photochemistry and Photopolymerization Activity of Novel 4-Alkylamino Benzophenone Initiators-Synthesis, Characterization, Spectroscopic and Photopolymerization Activity," European Polymer Journal, Pergamon Press, Ltd. Oxford, GB, vol. 26, No. 12, 1990, pp. 1345-1353, XP002393858.

* cited by examiner

*Primary Examiner*—Venkataraman Balasubramanian
(74) *Attorney, Agent, or Firm*—Scott D. Rothenberger; Fulbright & Jaworski

(57) ABSTRACT

The invention describes novel crosslinking compounds that include photoactivatable moieties. Several families of compounds are disclosed that can include one or more hydrophilic moieties that help to solubilize the compounds in aqueous environments.

23 Claims, No Drawings

PHOTOCHEMICAL CROSSLINKERS FOR POLYMER COATINGS AND SUBSTRATE TIE-LAYER

CROSS REFERENCE TO RELATED APPLICATIONS

This application claims benefit under 35 U.S.C. §119(e) to U.S. Ser. Nos. 60/690,018, entitled "Photochemical Crosslinkers for Polymer Coatings and Substrate Tie-Layer", filed Jun. 13, 2005, 60/709,330, entitled "Photochemical Crosslinkers for Polymer Coatings and Substrate Tie-Layer", filed Aug. 18, 2005 and 60/804,222, entitled "Photochemical Crosslinkers for Polymer Coatings and Substrate Tie-Layer", filed Jun. 8, 2006, the contents of which are incorporated herein by reference in their entirety.

FIELD OF THE INVENTION

The invention relates generally to cross linking agents that are generally hydrophilic and provide photoactivatable groups. The compounds are useful as surface coating agents alone or in combination with other target molecules such as polymers, biomolecules and the like.

BACKGROUND OF THE INVENTION

There exist many ways to coat, adhere, adsorb, modify, etc. a surface with a material, such that the material changes the characteristics of the surface. For example, suitable coatings can be prepared that when applied to a given surface render the surface hydrophobic. In other instances, the coating may provide enhanced ability to bind with a target molecule, such as a protein.

In particular, there are known crosslinking materials that include a latent reactive group, such as a photoactivatable group. The crosslinking material has, in general, at least two photoactivatable groups, such that one group can be activated and attached to the surface of the substrate. The remaining latent group, can then later be, or simultaneously with the surface attachment, activated to react with a target molecule such as a polymer or a biomolecule.

There are generally three types of crosslinking materials with photoactivatable groups. One type is hydrophobic in nature, making it difficult to dissolve in an aqueous systems. The second type is hydrophilic, but includes quaternary charged moieties. Quaternary compounds tend to promote non-specific binding of non-target molecules, which is often not a desired result. A third type of crosslinking material with photoactivatable groups includes negatively "charged" groups, such as carboxylic acids, sulfonic acids, phosphoric acids and the like. Although these materials are considered to be hydrophilic, they also increase non-specific binding interactions with non-targeted molecules by the crosslinking material.

Therefore, a need exists for a crosslinking material that includes photoactivatable groups that is hydrophilic in nature and does not promote non-specific binding interactions with non-target molecules.

BRIEF SUMMARY OF THE INVENTION

The present invention surprisingly provides unique crosslinking molecule families that include photoactivatable groups. The crosslinkers are hydrophilic in nature and do not promote non-specific binding interactions with non-target molecules.

One unique crosslinking molecular family includes compounds having the formula:

L is a linking group. D is O, S, SO, $SO_2$, $NR^5$ or $CR^6R^7$. T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond. $R^1$ is a hydrogen atom, an alkyl, alkyloxyalkyl, aryl, aryloxyalkyl or aryloxyaryl group. X is O, S, or $NR^8R^9$. P is a hydrogen atom or a protecting group, with the provisio that P is absent when X is $NR^8R^9$. $R^2$ is a hydrogen atom, an alkyl, alkyloxyalkyl, aryl, aryloxylalkyl or aryloxyaryl group. G is O, S, SO, $SO_2$, $NR^{10}$, $(CH_2)_t-O-$ or $C=O$. $R^3$ and $R^4$ are each independently an alkyl, aryl, arylalkyl, heteroaryl, or an heteroarylalkyl group, or optionally, $R^3$ and $R^4$ can be tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$, $(-CH_2-)_rS(O)_2(-CH_2-)_s$, or $(-CH_2-)_rNR(-CH_2-)_s$. $R^5$ and $R^{10}$ are each independently a hydrogen atom or an alkyl, aryl, or arylalkyl group. $R^6$ and $R^7$ are each independently a hydrogen atom, an alkyl, aryl, arylalkyl, heteroaryl or heteroarylalkyl group. $R^8$ and $R^9$ are each independently a hydrogen atom, an alkyl, aryl, or arylalkyl group, R is a hydrogen atom, an alkyl group or an aryl group, q is an integer from 1 to about 7, r is an integer from 0 to about 3, s is an integer from 0 to about 3, m is an integer from 2 to about 10, t is an integer from 1 to about 10 and x is an integer from 1 to about 500.

In one aspect, L is a branched or unbranched alkyl chain having between about 2 and about 10 carbon atoms.

In another aspect, D is an oxygen atom (O).

In still another aspect, T is $(-CH_2-)_x$ or $(-CH_2CH_2-O-)_x$ and x is 1 or 2.

In still yet another aspect, $R^1$ is a hydrogen atom.

In yet another aspect, X is an oxygen atom, O, and P is a hydrogen atom.

In another aspect, $R^2$ is a hydrogen atom.

In still another aspect, G is an oxygen atom, O.

In still yet another aspect, $R^3$ and $R^4$ are each individually aryl groups, which can be further substituted, and m is 3.

In one particular aspect, L is

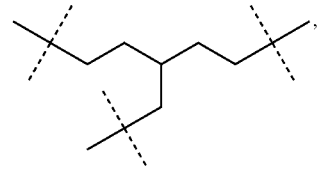

D is O, T is $(-CH_2-)_x$, $R^1$ is a hydrogen atom, X is O, P is a hydrogen atom, $R^2$ is a hydrogen atom, G is O, $R^3$ and $R^4$ are phenyl groups, m is 3 and x is 1.

In yet another particular aspect, L is $(-CH_2-)_y$, D is O, T is $(-CH_2-)_x$, $R^1$ is a hydrogen atom, X is O, P is a hydrogen atom, $R^2$ is a hydrogen atom, G is O, $R^3$ and $R^4$ are phenyl groups, m is 2, x is 1 and y is an integer from 2 to about 6, and in particular, y is 2, 4 or 6.

A second unique crosslinking molecular family includes compounds having the formula:

L is a linking group. T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond. $R^1$ is a hydrogen atom, an alkyl, alkyloxyalkyl, aryl, aryloxyalkyl or aryloxyaryl group. X is O, S, or $NR^8R^9$. P is a hydrogen atom or a protecting group, with the provisio that P is absent when X is $NR^8R^9$. $R^2$ is a hydrogen atom, an alkyl, alkyloxyalkyl, aryl, aryloxylalkyl or aryloxyaryl group. G is O, S, SO, $SO_2$, $NR^{10}$, $(CH_2)_t$—O— or C=O. $R^3$ and $R^4$ are each independently an alkyl, aryl, arylalkyl, heteroaryl, or an heteroarylalkyl group, or optionally, $R^3$ and $R^4$ can be tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$, $(-CH_2-)_rS(O)_2(-CH_2-)_s$, or $(-CH_2-)_rNR(-CH_2-)_s$. $R^{10}$ is a hydrogen atom or an alkyl, aryl, or arylalkyl group. $R^8$ and $R^9$ are each independently a hydrogen atom, an alkyl, aryl, or arylalkyl group. R is a hydrogen atom, an alkyl group or an aryl group, q is an integer from 1 to about 7, r is an integer from 0 to about 3, s is an integer from 0 to about 3, m is an integer from 2 to about 10, t is an integer from 1 to about 10 and x is an integer from 1 to about 500.

In one aspect, L has a formula according to structure (I):

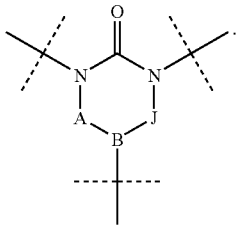

(I)

A and J are each independently a hydrogen atom, an alkyl group, an aryl group, or together with B form a cyclic ring, provided when A and J are each independently a hydrogen atom, an alkyl group, or an aryl group then B is not present, B is $NR^{11}$, O, or $(-CH_2-)_z$, provided when A, B and J form a ring, then A and J are $(-CH_2-)_z$ or C=O, $R^{11}$ is a hydrogen atom, an alkyl group, an aryl group or denotes a bond with T, each z independently is an integer from 0 to 3 and provided when either A or J is C=O, then B is $NR^{11}$, O, or $(-CH_2-)_z$ and z must be at least 1.

In another aspect T is $-CH_2-$.
In still another aspect, $R^1$ is a hydrogen atom.
In still yet another aspect, X is O and P is a hydrogen atom.
In still another aspect, $R^2$ is a hydrogen atom.
In yet another aspect, G is O.
In another aspect, $R^3$ and $R^4$ are each individually aryl groups.
In still yet another aspect, m is 3, and in particular, A and J are both C=O and B is N or A and J are both hydrogen atoms.

A third unique crosslinking molecular family includes compounds having the formula:

L-((TGQR$^3$C(=O)R$^4$))$_m$.

L is a linking group. T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond. G is O, S, SO, $SO_2$, $NR^{10}$, $(CH_2)_t$—O— or C=O. Q is $(-CH_2-)_p$, $(-CH_2CH_2-O-)_p$, $-(CH_2CH_2CH_2-O-)_p$ or $(-CH_2CH_2CH_2CH_2-O-)_p$. $R^3$ and $R^4$ are each independently an alkyl, aryl, arylalkyl, heteroaryl, or an heteroarylalkyl group, or optionally, $R^3$ and $R^4$ can be tethered together $(-CH_2-)_q$, $(-CH_2-)_rC=O(-CH_2-)_s$, $(-CH_2-)_rS(-CH_2-)_s$, $(-CH_2-)_rS=O(-CH_2-)_s$, $(-CH_2-)_rS(O)_2(-CH_2-)_s$, or $(-CH_2-)_rNR(-CH_2-)_s$. $R^{10}$ is a hydrogen atom or an alkyl, aryl, alkylaryl or arylalkyl group. R is a hydrogen atom, an alkyl group or an aryl group, q is an integer from 1 to about 7, r is an integer from 0 to about 3, s is an integer from 0 to about 3, m is an integer from 2 to about 10, p is an integer from 1 to about 10, t is an integer from 1 to about 10 and x is an integer from 1 to about 500.

In one aspect, L has a formula according to structure (I):

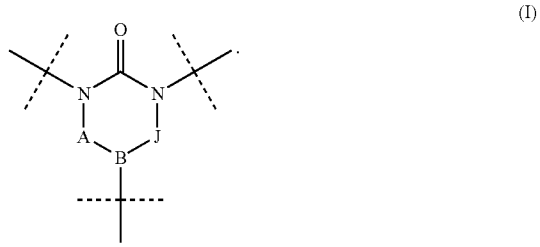

(I)

A and J are each independently a hydrogen atom, an alkyl group, an aryl group, or together with B form a cyclic ring, provided when A and J are each independently a hydrogen atom, an alkyl group, or an aryl group then B is not present, B is $NR^{11}$, O, or $(-CH_2-)_z$, provided when A, B and J form a ring, then A and J are $(-CH_2-)_z$ or C=O, $R^{11}$ is a hydrogen atom, an alkyl group, an aryl group or denotes a bond with T, each z independently is an integer from 0 to 3 and provided when either A or J is C=O, then B is $NR^{11}$, O, or $(-CH_2-)_z$ and z must be at least 1.

In one aspect, T is $-CH_2-$.
In another aspect, G is an oxygen atom, O.
In still another aspect, $R^3$ and $R^4$ are each individually aryl groups, which can be substituted, and m is 2.
In still yet another aspect, A and J are both C=O and B is $NR^{11}$.
In another aspect, A and J are both hydrogen atoms.
In yet another aspect, L has a formula according to structure (II):

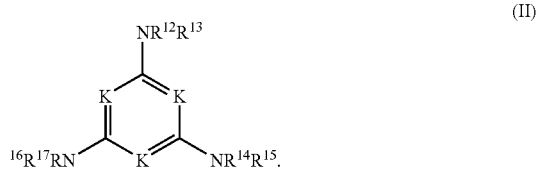

(II)

$R^{12}$, $R^{13}$, $R^{14}$, $R^{15}$, $R^{16}$, $R^{17}$ are each independently a hydrogen atom, an alkyl or aryl group or denotes a bond with T, provided at least two of $R^{12}$, $R^{13}$, $R^{14}$, $R^{15}$, $R^{16}$, $R^{17}$ are bonded with T and each K, independently is CH or N.

A fourth unique crosslinking molecular family includes compounds having the formula:

L-((GTZR$^3$C(=O)R$^4$))$_m$

L is a linking group. T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond. G is O, S, SO, $SO_2$, $NR^{10}$, $(CH_2)_t$—O— or C=O. Z can be a C=O, COO or CONH when T is $(-CH_2-)_x$. $R^3$ and $R^4$ are each independently an alkyl, aryl, arylalkyl, heteroaryl, or an heteroarylalkyl group, or optionally, $R^3$ and $R^4$ can be tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$, $(-CH_2-)_rS(O)_2(-CH_2-)_s$, or $(-CH_2-)_rNR(-CH_2-)_s$. $R^{10}$ is a hydrogen atom or an alkyl, aryl, alkylaryl or arylalkyl group. R is a hydrogen atom, an alkyl group or an aryl group, q is an integer from 1 to about 7, r is an integer from 0 to about 3, s is an integer from 0 to about 3, m is an integer from 2 to about 10, p is an integer from 1 to about 10, t is an integer from 1 to about 10 and x is an integer from 1 to about 500.

In one aspect, L has a formula according to structure (I):

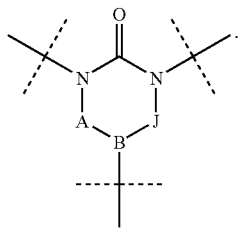

(I)

A and J are each independently a hydrogen atom, an alkyl group, an aryl group, or together with B form a cyclic ring, provided when A and J are each independently a hydrogen atom, an alkyl group, or an aryl group then B is not present, B is $NR^{11}$, O, or $(-CH_2-)_z$, provided when A, B and J form a ring, then A and J are $(-CH_2-)_z$ or $C=O$, $R^{11}$ is a hydrogen atom, an alkyl group, an aryl group or denotes a bond with T, each z independently is an integer from 0 to 3 and provided when either A or J is $C=O$, then B is $NR^{11}$, O, or $(-CH_2-)_z$ and z must be at least 1.

In one aspect, T is $-CH_2-$.

In another aspect, G is an oxygen atom, O.

In still another aspect, $R^3$ and $R^4$ are each individually aryl groups, which can be substituted, and m is 2.

In still yet another aspect, A and J are both $C=O$ and B is $NR^{11}$.

In another aspect, A and J are both hydrogen atoms.

In yet another aspect, L has a formula according to structure (II):

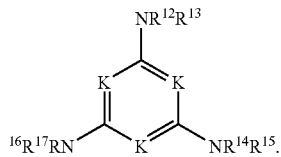

(II)

$R^{12}$, $R^{13}$, $R^{14}$, $R^{15}$, $R^{16}$, $R^{17}$ are each independently a hydrogen atom, an alkyl or aryl group or denotes a bond with T, provided at least two of $R^{12}$, $R^{13}$, $R^{14}$, $R^{15}$, $R^{16}$, $R^{17}$ are bonded with T and each K, independently is CH or N.

In still yet another aspect, compounds of the present invention provide that $R^3$ and $R^4$ are both phenyl groups and are tethered together via a CO, a S or a $CH_2$.

In yet another aspect, compounds of the present invention provide when $R^3$ and $R^4$ are both phenyl group, the phenyl groups can be substituted with at least one $CH_3OCH_{2\ CH2}O-$.

The compounds of the invention have broad applications. The compounds can be used in surface modifications. The use of hydrophilic groups provide the compounds with water solubility. This physical attribute provides that the compositions can be used where water soluble agents are favored.

The inclusion of photoreactive moieties within the compositions provides that the composition can be used with a wide range of support surfaces. The compositions can be used alone or in combination with other materials to provide a desired surface characteristic. The compositions, alone or in combination with another material, provides the treated surface having a modified property that can include lubricity, hemocompatability, wettability, hydrophilicity, biocompatibility and/or bacterial adhesion.

In another aspect, the present invention pertains to lubricious compositions that include polyvinylpyrrolidone and one or more of the crosslinkers described herein.

In yet another aspect, the present invention pertains to reaction products formed between polyvinylpyrrolidone and the crosslinkers described herein. The reaction product can be a coating that can advantageously be used to coat catheters and medical devices, providing a surface that is lubricious and remains moist.

In still yet another aspect, the combination of one or more crosslinkers described herein and polyvinylpyrrolidone can be combined to form a coating mixture that can be subjected to photoactivation. This can be performed on various surfaces, and in particular, on one or more surfaces of a catheter.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

The present invention surprisingly provides unique crosslinking molecule families that include photoactivatable groups. The crosslinkers are hydrophilic in nature and do not promote non-specific binding interactions with non-target molecules.

The compounds of the invention are useful as coating agents. The compounds are derived from three different types of molecular families. Each family includes one or more hydrophilic portions, i.e., a hydroxyl group (that may be protected), amines, alkoxy groups, etc. In one embodiment the family has the formula:

$$L-((D-T-C(R^1)(XP)CHR^2GR^3C(=O)R^4))_m.$$

L is a linking group. D is O, S, SO, $SO_2$, $NR^5$ or $CR^6R^7$. T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond. $R^1$ is a hydrogen atom, an alkyl, alkyloxyalkyl, aryl, aryloxyalkyl or aryloxyaryl group. X is O, S, or $NR^8R^9$. P is a hydrogen atom or a protecting group, with the provisio that P is absent when X is $NR^8R^9$. $R^2$ is a hydrogen atom, an alkyl, alkyloxyalkyl, aryl, aryloxylalkyl or aryloxyaryl group. G is O, S, SO, $SO_2$, $NR^{10}$, $(CH_2)_t-O-$ or $C=O$. $R^3$ and $R^4$ are each independently an alkyl, aryl, arylalkyl, heteroaryl, or a heteroarylalkyl group, or optionally, $R^3$ and $R^4$ can be tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$, $(-CH_2-)_rS(O)_2(-CH_2-)_s$, or $(-CH_2-)_rNR(-CH_2-)_s$. $R^5$ and $R^{10}$ are each independently a hydrogen atom or an alkyl, aryl, or arylalkyl group. $R^6$ and $R^7$ are each independently a hydrogen atom, an alkyl, aryl, arylalkyl, heteroaryl or heteroarylalkyl group. $R^8$ and $R^9$ are each independently a hydrogen atom, an alkyl, aryl, or arylalkyl group, R is a hydrogen atom, an alkyl group or an aryl group, q is an integer from 1 to about 7, r is an integer from 0 to about 3, s is an integer from 0 to about 3, m is an integer from 2 to about 10, t is an integer from 1 to about 10 and x is an integer from 1 to about 500.

In one aspect, L is a branched or unbranched alkyl chain having between about 2 and about 10 carbon atoms.

In another aspect, D is an oxygen atom (O).

In still another aspect, T is (—CH$_2$—)$_x$ or (—CH$_2$CH$_2$—O—)$_x$ and x is 1 or 2.

In still yet another aspect, R$^1$ is a hydrogen atom.

In yet another aspect, X is an oxygen atom, O, and P is a hydrogen atom.

In another aspect, R$^2$ is a hydrogen atom.

In still another aspect, G is an oxygen atom, O.

In still yet another aspect, R$^3$ and R$^4$ are each individually aryl groups, which can be further substituted, and m is 3.

In one particular aspect, L is

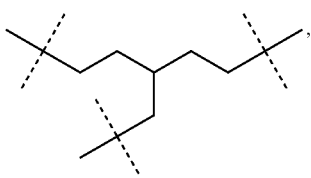

D is O, T is (—CH$_2$—)$_x$, R$^1$ is a hydrogen atom, X is O, P is a hydrogen atom, R$^2$ is a hydrogen atom, G is O, R$^3$ and R$^4$ are phenyl groups, m is 3 and x is 1.

In yet another particular aspect, L is (—CH$_2$—)$_y$, D is O, T is (—CH$_2$—)$_x$, R$^1$ is a hydrogen atom, X is O, P is a hydrogen atom, R$^2$ is a hydrogen atom, G is O, R$^3$ and R$^4$ are phenyl groups, m is 2, x is 1 and y is an integer from 2 to about 6, and in particular, y is 2, 4 or 6.

In certain embodiments, x is an integer from about 1 to about 500, more particularly from about 1 to about 400, from about 1 to about 250, from about 1 to about 200, from about 1 to about 150, from about 1 to about 100, from about 1 to about 50, from about 1 to about 25 or from about 1 to about 10

In another embodiment, the family has the formula:

wherein L, T, R$^1$, X, P, R$^2$, G, R$^3$, R$^4$, R$^8$, R$^9$, R$^{10}$, R, q, r, s, m, t and x are as defined above.

In one aspect, L has a formula according to structure (I):

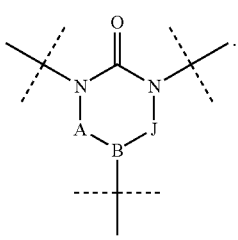

(I)

A and J are each independently a hydrogen atom, an alkyl group, an aryl group, or together with B form a cyclic ring, provided when A and J are each independently a hydrogen atom, an alkyl group, or an aryl group then B is not present, B is NR$^{11}$, O, or (—CH$_2$—)$_z$, provided when A, B and J form a ring, then A and J are (—CH$_2$—)$_z$ or C=O, R$^{11}$ is a hydrogen atom, an alkyl group, an aryl group or denotes a bond with T, each z independently is an integer from 0 to 3 and provided when either A or J is C=O, then B is NR$^{11}$, O, or (—CH$_2$—)$_z$ and z must be at least 1.

In another aspect T is —CH$_2$—.

In another embodiment, the family has the formula:

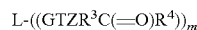

wherein L, T, G, R$^3$, R$^4$, R$^{10}$, R, q, r, s, m, t and x are as defined above. Z can be a C=O, COO or CONH when T is (—CH$_2$—)$_x$.

In one aspect, L has a formula according to structure (I):

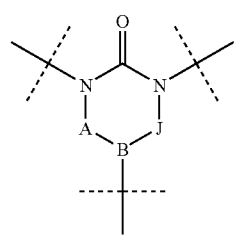

(I)

wherein A, B, J, R$^{11}$, and z are as defined above.

In another aspect, L has a formula according to structure (II):

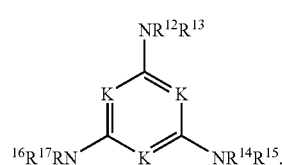

(II)

R$^{12}$, R$^{13}$, R$^{14}$, R$^{15}$, R$^{16}$, R$^{17}$ are each independently a hydrogen atom, an alkyl or aryl group or denotes a bond with T, provided at least two of R$^{12}$, R$^{13}$, R$^{14}$, R$^{15}$, R$^{16}$, R$^{17}$ are bonded with T and each K, independently is CH or N.

In another embodiment, the family has the formula:

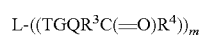

wherein L, G, R$^3$, R$^4$, R$^{10}$, R, q, r, s, m, t and x are as defined above. T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond. Q is (—CH$_2$—)$_p$, (—CH$_2$CH$_2$—O—)$_p$, (—CH$_2$CH$_2$CH$_2$—O—)$_p$ or (—CH$_2$CH$_2$CH$_2$CH$_2$—O—)$_p$ and p is an integer from 1 to about 10.

In one aspect, L has a formula according to structure (I):

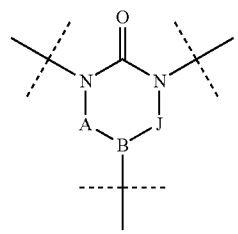

(I)

wherein A, B, J, R$^{11}$, and z are as defined above.

In another aspect, L has a formula according to structure (II):

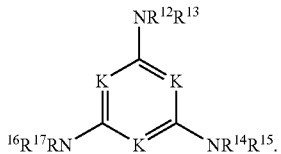
(II)

$R^{12}$, $R^{13}$, $R^{14}$, $R^{15}$, $R^{16}$, $R^{17}$ are each independently a hydrogen atom, an alkyl or aryl group or denotes a bond with T, provided at least two of $R^{12}$, $R^{13}$, $R^{14}$, $R^{15}$, $R^{16}$, $R^{17}$ are bonded with T and each K, independently is CH or N.

In still yet another aspect, compounds of the present invention provide that $R^3$ and $R^4$ are both phenyl groups and are tethered together via a CO, a S or a $CH_2$.

In yet another aspect, compounds of the present invention provide when $R^3$ and $R^4$ are phenyl groups, the phenyl groups can each independently be substituted with at least one alkyloxyalkyl group, such as $CH_3O$—$(CH_2CH_2O$—$)_n$—, or $CH_3O(—CH_2CH_2CH_2O—)_n$-a hydroxylated alkoxy group, such as HO—$CH_2CH_2O$—, HO(—$CH_2CH_2O$—$)_n$— or HO(—$CH_2CH_2CH_2O$—$)_n$—, etc. wherein n is an integer from 1 to about 10.

In another embodiment the family has the formula:

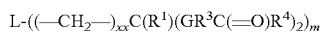

wherein L, each R, $R^1$, each G, each $R^3$, each $R^4$, each $R^{10}$, each q, each r, each s, each t and m are as defined above and xx is an integer from 1 to about 10.

In one aspect, L has a formula according to structure (I):

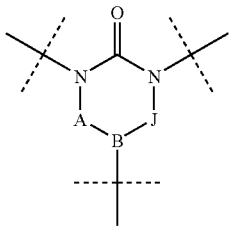
(I)

wherein A, B, J, $R^{11}$, and z are as defined above.

In another aspect, A and B are both hydrogen atoms.
In still another aspect, xx is 1.
In yet another aspect, $R^1$ is H.
In still yet another aspect, G is (—$CH_2$—$)_tO$— and t is 1.
In another aspect, $R^3$ and $R^4$ are each individually aryl groups.

In still yet another embodiment, xx is 1, $R^1$ is H, each G is (—$CH_2$—$)_tO$—, t is 1 and each of $R^3$ and $R^4$ are each individually aryl groups.

In another embodiment of the invention, the family has the formula

where L, R, $R^1$, $R^2$, $R^3$, $R^4$, $R^8$, $R^9$, $R^{10}$, X, P, G, q, r, s, t, and m are as defined above.

In one aspect, L is

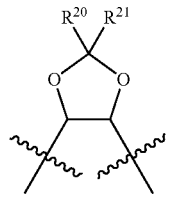

and $R^{20}$ and $R^{21}$ are each individually a hydrogen atom, an alkyl group or an aryl group.
In another aspect, $R^1$ is H.
In still another aspect, wherein X is O.
In yet another aspect, P is H.
In still yet another aspect, $R^2$ is H.
In another aspect, G is (—$CH_2$—)tO— and t is 1.
In still another aspect, $R^3$ and $R^4$ are each individually aryl groups.

In yet another aspect, $R^1$ is H, X is O, P is H, $R^2$ is H, G is (—$CH_2$—$)_tO$—, t is 1, $R^3$ and $R^4$ are each individually aryl groups and $R^{20}$ and $R^{21}$ are both methyl groups.

In yet another embodiment, the present invention provides a family of compounds having the formula:

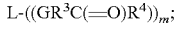

where L, G, R. $R^3$, $R^4$, $R^{10}$, q, r, s, m and t are as defined above.

In one aspect, L is

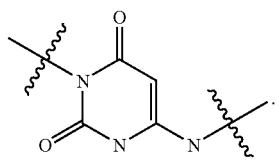

In another aspect, G is C=O.
In still another aspect, $R^3$ and $R^4$ are each individually aryl groups.
In yet another aspect, G is C=O and $R^3$ and $R^4$ are each individually aryl groups.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to alkyl groups having from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkyloxyalkyl" refers to a moiety having two alkyl groups tethered together via an oxygen bond. Suitable alkyloxyalkyl groups include polyoxyalkylenes, such as polyethyleneoxides, polypropyleneoxides, etc. that are terminated with an alkyl group, such as a methyl group. A general formula for such compounds can be depicted as R'—(OR")$_n$ or (R'O)$_n$—R" wherein n is an integer from 1 to about 10, and R' and R" are alkyl or alkylene groups.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group having from 1 to 6 carbon atoms. In preferred embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Aryloxyalkyl" refers to a moiety having an aryl group and an alkyl group tethered together via an oxygen bond. Suitable aryloxyalkyl groups include phenyloxyalkylenes, such as methoxyphenyl, ethoxyphenyl, etc.

"Cycloalkyl" by itself or as part of another substituent refers to a cyclic version of an "alkyl" group. Typical cycloalkyl groups include, but are not limited to, cyclopropyl; cyclobutyls such as cyclobutanyl and cyclobutenyl; cyclopentyls such as cyclopentanyl and cycloalkenyl; cyclohexyls such as cyclohexanyl and cyclohexenyl; and the like.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Heteroalkyl, Heteroalkanyl, Heteroalkenyl, Heteroalkynyl" by itself or as part of another substituent refer to alkyl, alkanyl, alkenyl and alkynyl radical, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$— and the like, where R' is hydrogen, alkyl, substituted alkyl, cycloalkyl, substituted cycloalkyl, aryl or substituted aryl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, benzoxazine, benzimidazole, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Hydroxyalkyl" by itself or as part of another substituent refers to an alkyl group in which one or more of the hydrogen atoms are replaced with a hydroxyl substituent. Thus, the term "hydroxyalkyl" is meant to include monohydroxyalkyls, dihydroxyalkyls, trihydroxyalkyls, etc.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Parent Heteroaromatic Ring System" refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Leaving group" is a group that is displaced during a reaction by a nucleophilic reagent. Suitable leaving groups include S(O)$_2$Me, —SMe or halo (e.g., F, Cl, Br, I).

"Linking group" is a group that serves as an intermediate locus between two or more end groups. The nature of the linking group can vary widely, and can include virtually any combination of atoms or groups useful for spacing one molecular moiety from another. For example, the linker may be an acyclic hydrocarbon bridge (e.g., a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH$_2$—, —CH$_2$—O—CH$_2$—, —O—CH=CH—

CH$_2$—, and the like), a monocyclic or polycyclic heteroaryl bridge (e.g., [3,4]furano, pyridino, thiopheno, piperidino, piperazino, pyrazidino, pyrrolidino, and the like) or combinations of such bridges.

"Protecting group" is a group that is appended to, for example, a hydroxyloxygen in place of a labile hydrogen atom. Suitable hydroxylprotecting group(s) include esters (acetate, ethylacetate), ethers (methyl, ethyl), ethoxylated derivatives (ethylene glycol, propylene glycol) and the like that can be removed under either acidic or basic conditions so that the protecting group is removed and replaced with a hydrogen atom. Guidance for selecting appropriate protecting groups, as well as synthetic strategies for their attachment and removal, may be found, for example, in Greene & Wuts, *Protective Groups in Organic Synthesis,* 3d Edition, John Wiley & Sons, Inc., New York (1999) and the references cited therein (hereinafter "Greene & Wuts").

The compounds of the invention that can be used as coating agents include one or more moieties that render the molecule hydrophilic in nature. In certain aspects, the hydrophilic portion is a hydroxyl or protected hydroxyl group. Alternatively, the molecule can include amine functionality and/or an alkoxy group or polyalkyoxy group. The type and number of hydrophilic groups in a coating agent are sufficient to provide the agent with a water solubility (at room temperature and optimal pH) of at least about 0.1 mg/ml, in particular at least about 0.5 mg/ml, and more particularly at least about 1 mg/ml. Given the nature of the surface coating process, coating agent solubility levels of at least about 0.1 mg/ml are generally adequate for providing useful coatings of target molecules (e.g., polymer layers) on surfaces.

The compositions of the present application can thus be contrasted with other coating agents in the art, which are typically considered to be insoluble in water (e.g., having a comparable water solubility in the range of about 0.1 mg/ml or less, and more often about 0.01 mg/ml or less). For this reason, conventional coating agents are typically provided and used in solvent systems in which water is either absent or is provided as a minor (e.g., less than about 50% by volume) component.

Alternatively, the compositions of the invention can be solubilized in water/alcohol solutions or in alcohols, such as isopropanol, butanol, methanol, ethanol, cellosolves (glycols), and the like.

Examples of moieties that help to provide hydrophilicity to the compositions of the invention are as described above and include hydroxyl groups, polyhydric groups, alkoxy groups, polyoxyalkylenes, amines, amides and esters.

Photoreactive species are as described herein, and are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") in particular.

Photoreactive species respond to external stimuli and undergo active specie generation with the formation of a covalent bond to an adjacent chemical structure, e.g., as provided by the same or a different molecule. Photoreactive species are those groups of atoms in a molecule that retain their covalent bonds during storage but, upon activation by an external energy source, form covalent bonds with other molecules.

Photoreactive species generate active species such as free radicals and particularly nitrenes, carbenes, and excited states of ketones upon absorption of electromagnetic energy. Photoreactive species can be chosen to be responsive to various portions of the electromagnetic spectrum, and photoreactive species that are responsive to e.g., ultraviolet and visible portions of the spectrum, are referred to as a "photochemical group" or "photogroup."

The use of photoreactive species in the form of photoreactive aryl ketones are useful, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. In particular, thioxanthone, and its derivatives, having excitation energies greater than about 360 nm are useful.

The functional groups of such ketones are preferred since they are readily capable of undergoing an activation/inactivation/reactivation cycle. Benzophenone is a photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased coating efficiency.

The compositions of the invention can be applied to a surface of interest in any suitable manner. For example, the composition can be applied by dip coating or by dispersing the compound on the surface (for example, by spray coating). Suitable methods of application include application in solution, dipping, spray coating, knife coating, and roller coating. In one aspect, the compound is applied to the surface via spray coating, as this application method provides increased density of the compound on the support surface, thereby improving durability.

Linking agents can be used in any suitable manner, including by the simultaneous or sequential attachment of a chemical compound to a surface. Linking agents of the present invention can be used to modify any suitable surface. Where the latent reactive group of the agent is a photoreactive group of the preferred type, it is particularly preferred that the surface provide abstractable hydrogen atoms suitable for covalent bonding with the activated group.

Plastics such as polyolefins, polystyrenes, poly(methyl) methacrylates, polyacrylonitriles, poly(vinylacetates), poly (vinyl alcohols), chlorine-containing polymers such as poly (vinyl) chloride, polyoxymethylenes, polycarbonates, polyamides, polyimides, polyurethanes, phenolics, amino-epoxy resins, polyesters, silicones, cellulose-based plastics, and rubber-like plastics can all be used as supports, providing surfaces that can be modified as described herein. See generally, "Plastics", pp. 462-464, in Concise Encyclopedia of Polymer Science and Engineering, Kroschwitz, ed., John Wiley and Sons, 1990, the disclosure of which is incorporated herein by reference. In addition, supports such as those formed of pyrolytic carbon, parylene coated surfaces, and silylated surfaces of glass, ceramic, or metal are suitable for surface modification.

The method of the present invention involves the attachment of a target molecule to a support surface by use of the compounds of the invention. For example, a compound of the invention is provided having two or more photoactivatable groups in the presence of a support surface. A portion of the photoactivatable groups are activated and covalently bonded to the surface. A portion of the photoactivatable groups are allowed to revert to their inactive state and are later reactivated in order to later bind a target molecule in order to attach the target molecule to the surface.

The steps of the method can be performed in any suitable order. For example, a multifunctional compound as described herein can be physically absorbed or adsorbed to a suitable support surface by hydrophobic interactions. Upon illumination, a portion of the photoreactive groups (e.g., benzophenone groups) undergo covalent bond formation at the support surface by the aforementioned mechanism. With the absence of abstractable hydrogens in the proximity of the remaining unbonded photoreactive group(s), and removal of the illumination source, the excited state benzophenone returns to ground state energy. These remaining groups are then capable of being reactivated when the target molecule intended for immobilization is present and when the treated surface is exposed to another round of illumination. This method can be described as a "two-step" approach, where the photoreactive reagent is applied in the first step to create the latent reactive surface, and in the second step, the target molecule is added for attachment to the activated surface.

Alternatively, the method, described as a "one-step" method, provides that the compound of the present invention is mixed in solution together with the target molecule to form a composition. The resultant composition is used to surface modify materials in a single illumination step. In this case, illumination triggers not only covalent bond formation of the latent photoreactive group with the material surface, but also simultaneously triggers covalent bond formation with adjacent target molecules residing on the surface.

In an alternative embodiment, the composition and the target molecule can be combined together in a one step process simultaneously with illumination.

In another alternative method, a compound of the invention is used to pretreat a substrate surface prior to the application and bonding of molecules that have themselves been functionalized with latent reactive groups. This method is useful in situations where a particularly difficult substrate requires maximal coating durability. In this manner, the number of covalent bonds formed between the substrate surface and the target molecule derivatized with latent reactive groups can typically be increased, as compared to surface modification with a desired latent reactive group-containing target molecule alone.

Suitable target molecules for use in the present invention, for attachment to a support surface, encompass a diverse group of substances. Target molecules can be used in either an underivatized form or previously derivatized. Moreover, target molecules can be immobilized singly or in combination with other types of target molecules.

Target molecules can be immobilized to the surface either after (e.g., sequentially) the surface has been primed with linking agent. Alternatively, however, target molecules are immobilized during (e.g., simultaneously with) attachment of the present linking agent to the surface.

Typically, target molecules are selected so as to confer particular desired properties to the surface and/or to the device or article bearing the surface. Examples of suitable target molecules, and the surface properties they are typically used to provide, is represented by the following nonlimiting list:

| TARGET MOLECULE | FUNCTIONAL ACTIVITY |
|---|---|
| Synthetic Polymers | |
| Sulfonic acid-substituted polyacrylamide | Lubricity, negatively charged surface, hydrophilicity |
| Polyacrylamide | Lubricity, protein repulsion, hydrophilicity |
| Polyethylene glycol | Lubricity, cell and protein repulsion, hydrophilicity |
| Polyethyleneimine | Positively charged surface |
| Polylactic acid | Bioerodible surface |
| Polyvinyl alcohol | Lubricity, hydrophilicity |
| Polyvinyl pyrrolidone | Lubricity, hydrophilicity |
| Quaternary amine-substituted polyacrylamide | Lubricity, positively charged surface |
| Silicone | Lubricity, hydrophobicity |
| Conductive polymers, e.g., polyvinylpyridine, polyacetylene, polypyrrole) | Electric conductivity |
| Carbohydrates | |
| Alginic acid | Lubricity, hydrophilicity |
| Cellulose | Lubricity, hydrophilicity, biodegradable glucose source |
| Chitosan | Positively charged surface, hydrophilicity |
| Glycogen | Hydrophilicity, biodegradable glucose source |
| Heparin | Antithrombogenicity, hydrophilicity, cell attachment |
| Hyaluronic acid | Lubricity, negatively charged surface |
| Pectin | Lubricity, hydrophilicity |
| Mono-, di-saccharides | Hydrophilicity |
| Dextran sulfate | Chromatography media |
| Proteins | |
| Antibodies | Antigen binding |
| Antithrombotic agents (e.g., antithrombin III) | Antithrombogenic surface |
| Albumin | Nonthrombogenic surface |
| Attachment proteins/peptides (e.g. collagen) | Cell attachment |
| Enzymes | Catalytic surfaces |
| Extracellular matrix proteins/peptides | Cell attachment and growth |
| Growth factors, proteins/peptides | Cell growth |
| Hirudin | Antithrombogenic surface |
| Thrombolytic proteins (e.g., streptokinase, plasmin, urokinase) | Thrombolytic activity |
| Lipids | |
| Fatty acids | Hydrophobicity, biocompatibility |
| Mono-, di- and triglycerides | Hydrophobicity, lubricity, biodegradable fatty acid source |
| Phospholipids | Hydrophobicity, lubricity, biodegradable fatty acid source |
| Prostaglandins/leukotrienes | Nonthrombogenic surface/immobilized messengers |
| Nucleic Acids | |
| DNA | Substrate for nucleases/affinity binding |
| RNA | Substrate for nucleases/affinity binding |
| Nucleosides, nucleotides | Source of purines, pyrimidines, enzyme cofactors |
| Drugs/vitamins/cofactors | |
| Enzyme cofactors | Immobilized enzymes |
| Heme compounds | Globin bindings/surface oxygenation |
| Drugs | Drug activity |
| Nonpolymeric Materials | |
| Dyes (e.g., azo dyestuffs) | Coloring agents |
| Fluorescent compounds (e.g., fluorescein) | Fluorescence |

In one embodiment, the compounds of the invention can be applied to a catheter to provide a lubricious coating.

Medical articles that can be fabricated from or coated or treated with the compounds of the invention include, but are not limited to, catheters including urinary catheters and vascular catheters (e.g., peripheral and central vascular catheters), wound drainage tubes, arterial grafts, soft tissue patches, gloves, shunts, stents, tracheal catheters, wound dressings, sutures, guide wires and prosthetic devices (e.g., heart valves and LVADs). Vascular catheters which can be prepared according to the present invention include, but are not limited to, single and multiple lumen central venous catheters, peripherally inserted central venous catheters, emergency infusion catheters, percutaneous sheath introducer systems, thermodilution catheters, including the hubs and ports of such vascular catheters, leads to electronic devices such as pacemakers, defibrillators, artificial hearts, and implanted biosensors.

The present invention provides to lubricious compositions that include one or more hydrophilic polymer(s), such as those listed throughout the specification, i.e., polyvinylpyrrolidone, polyacrylamide, hyaluronic acid, and/or chitosan, and one or more of the crosslinkers described herein.

In yet another aspect, the present invention pertains to reaction products formed between one or more hydrophilic polymer(s), i.e., polyvinylpyrrolidone, and the crosslinkers described herein. The reaction product can be a coating that can advantageously be used to coat catheters and medical devices, providing a surface that is lubricious and remains moist.

The combination of one or more crosslinkers described herein and one or more hydrophilic polymer(s), such as polyvinylpyrrolidone can be combined to form a coating mixture. This mixture can be subjected to photoactivation. The activation can be performed on various surfaces, and in particular, on one or more surfaces of a catheter.

The hydrophilic polymer(s) that can be combined with one or more of crosslinkers of the invention can have a broad range of molecular weights. Advantageously, hydrophilic polymers such as PVP can be selected that include both high molecular weight components as well as low molecular weight components. For example, BASF provides several different PVPs including K30, K90, K12, K25 and K17. The number indicates MW in 1000s. Ranges of formulations were prepared from 50-50 K90/K30 to 90-10 K90/K30, with the higher the K90 the longer the dry time of the coating. For example, PVP's can be formulated from available molecular weight ranges that include >75% high molecular weight PVP (90K) and <25% low molecular weight PVP (30K).

In another embodiment, the compounds of the invention can be applied to a microscope slide or "chip" for biomolecule immobilization.

Compounds encompassed by the present invention can be prepared by selection of an appropriate aryl group with a photoactivatable group and at least one group that can either act as a nucleophilic site or can be acted upon in a nucleophilic displacement reaction with a linking agent (L) having at least two opposing groups, either a leaving group(s) or a nucleophilic group(s). General synthetic schemes detailed below demonstrate two approaches suitable to prepare compounds of the invention.

Scheme I

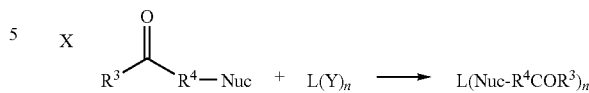

or

Scheme II

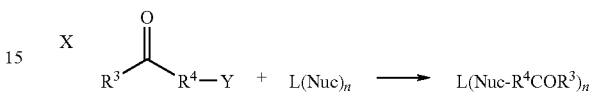

wherein X is an integer equivalent to "n" and n is an integer between 2 and about 6, $R^3$ and $R^4$ are as defined above, "Y" is a leaving group or a group that can be acted upon by a nucleophilic group, such as an ester, carboxylic acid halide, etc. and "Nuc" is a nucleophilic group, as described in further detail below. Alternatively, the reaction between "Y" and "Nuc" can be a condensation reaction, such as the reaction between, for example, a hydroxyl group and a carboxylic acid.

It should be understood in schemes I and II, that $R^3$ and $R^4$ are interchangeable.

Suitable nucleophilic groups (Nuc) include, for example, amines, hydroxyl, thiol, etc.

Suitable leaving groups, or groups susceptible to nucleophilic attack, include esters, ethers, epoxides, halides, isocyanates, isothiocyanates, sulfonyl chlorides, anhydrides, carboxylic acid halides, carboxylic acid esters, and aldehydes.

Resultant functional moieties from the reaction between the nucleophilic group and leaving (or condensation group) include, for example, esters, ethers, carbamates, thiocarbamates, sulfones, amides, ureas, thiourea, amines, sulfonamides, imines (that can be further reduced with a reducing agent such as sodium borohydride to an amine), etc.

Suitable reaction conditions for such condensations or nucleophilic displacements are known in the art. For example, hydroxyl containing moieties can be condensed with a carboxylic acid under dehydrating conditions (refluxing toluene, acid catalyst, Dean Stark trap) to form esters. Reactive halides can be displaced by hydroxyl groups under basic conditions. An isocyanate reacts with a hydroxyl group with heat to form carbamates. Likewise, an isothiocyanates reacts with a hydroxyl group to form a thiocarbamate. Under deprotonation conditions, a hydroxide ion reacts with an epoxide to form an ether linkage and forming a new hydroxyl group. Reaction between a hydroxyl and a sulfonyl chloride forms a sulfone. Reaction between a hydroxyl and an anhydride will form a ester with a carboxylic acid portion as well. Reaction between a hydroxyl group and an ester will also form an ester, with the removal of a corresponding displaced alcohol, generally under conditions that drive off the displaced alcohol.

Much like the reactions with hydroxyl groups, amines serve in similar manner. For example, an amine can react with an activated carboxylic acid for form an amide. Activation of a carboxylic acid can be facilitated by various methods in the art, including for example, use of dicyclohexylcarbodiimide (DCC) that generates urea as a side product. An isocyanate reacts with an amine to form a urea and an isothiocyanate reacts with an amine to form a thiourea.

Reaction between an amine and an epoxide will form an amine with an appended hydroxyl group from the nucleophilic displacement of the epoxide ring. Reaction between an amine and a sulfonyl chloride will form a sulfonamide. Reaction between an anhydride and an amine will afford an amide with a carboxylic portion attached to the product. Reaction between an aldehyde and an amine will form an imine which can be further reduced to an amine. Reaction between a carboxylic acid halide and an amine will form an amide, as well as the reaction between a carboxylic ester and amine. Lastly, melamine type compounds can react with an amine to form amine linkages.

Reaction conditions to form the compounds of the invention are known in the art. For example, suitable reaction conditions are described in "March's Advanced Organic Chemistry: Reactions, Mechanisms, and Structure, 5th Edition, John Wiley & Sons, Michael B. Smith & Jerry March; Fieser and Fieser's Reagents for Organic Synthesis" John Wiley & Sons, NY; Vogel's Textbook of Practical Organic Chemistry (Fifth Edition) by A. I. Vogel, B. S. Fumiss, A. J. Hannaford, P. W. G. Smith, and A. R. Tatchell, Longman Scientific and Technical, Longman Group UK; and Advanced Organic Chemistry parts A and B" Third Edition, F. A. Carey, R. S. Sundberg, Plenum Press, NY, 1990, the contents of which are incorporated herein by reference in their entirety.

It should also be understood that each "Y" independently can be different. Therefore, it is possible to have reaction products that include an ether linkage as well as an ester linkage to the carbonyl containing photoactivatable group.

An exemplary non-limiting reaction is depicted in Scheme III, in which a hydroxyl group undergoes nucleophilic addition to an ester or acid halide or can undergo a condensation reaction between the hydroxyl group and a carboxylic acid.

Scheme III

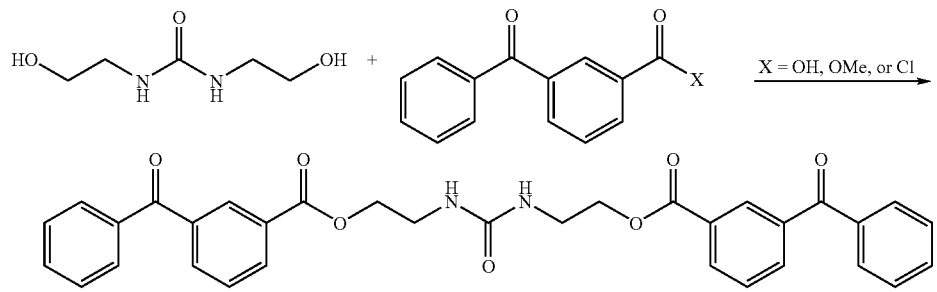

In a first embodiment, the present invention pertains to a compound comprising a formula:

L-((D-T-C(R$^1$)(XP)CHR$^2$GR$^3$C(=O)R$^4$))$_m$ wherein L is a linking group;

D is O, S, SO, SO$_2$, NR$^5$ or CR$^6$R$^7$;

T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;

R$^1$ is a hydrogen atom, an alkyl, alkyloxyalkyl, aryl, aryloxyalkyl or aryloxyaryl group;

X is O, S, or NR$^8$R$^9$;

P is a hydrogen atom or a protecting group, with the proviso that P is absent when X is NR$^8$R$^9$;

R$^2$ is a hydrogen atom, an alkyl, alkyloxyalkyl, aryl, aryloxyalkyl or aryloxyaryl group;

G is O, S, SO, SO$_2$, NR$^{10}$, (CH$_2$)$_t$—O— or C=O;

R$^3$ and R$^4$ are each independently an alkyl, aryl, arylalkyl, heteroaryl, or an heteroarylalkyl group or, optionally, R$^3$ and R$^4$ can be tethered together via (—CH$_2$—)$_q$, (—CH$_2$—)$_r$ C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R$^5$ and R$^{10}$ are each independently a hydrogen atom or an alkyl, aryl or arylalkyl group;

R$^6$ and R$^7$ are each independently a hydrogen atom, an alkyl, aryl, arylalkyl, heteroaryl or heteroarylalkyl group;

R$^8$ and R$^9$ are each independently a hydrogen atom, an alkyl, aryl, or arylalkyl group;

R is a hydrogen atom, an alkyl or an aryl group;

q is an integer from 1 to about 7;

r is an integer from 0 to about 3;

s is an integer from 0 to about 3;

m is an integer from 2 to about 10;

t is an integer from 1 to about 10; and x is an integer from 1 to about 500.

In a second embodiment of the first embodiment, L is a branched or unbranched alkyl chain having between about 2 and about 10 carbon atoms.

In a third embodiment of either of the first or second embodiments, D is O.

In a fourth embodiment of any of the first through third embodiments, T is (—CH$_2$—)$_x$ or (—CH$_2$CH$_2$—O—)$_x$ and x is 1 or 2.

In a fifth embodiment of the any of the first through fourth embodiments, R$^1$ is a hydrogen atom.

In a sixth embodiment of any of the first through fifth embodiments, X is O and P is a hydrogen atom.

In a seventh embodiment of any of the first through the sixth embodiments, R$^2$ is a hydrogen atom.

In an eighth embodiment of any of the first through the seventh embodiments, G is O.

In a ninth embodiment of any of the first through the eighth embodiments, R$^3$ and R$^4$ are each individually aryl groups.

In a tenth embodiment of any of the first through the ninth embodiments, m is 3.

In an eleventh embodiment of the first embodiment, L is

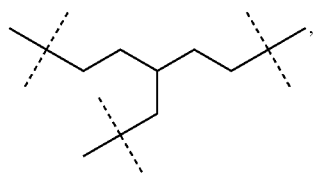

D is O, T is (—CH$_2$—)$_x$, R$^1$ is a hydrogen atom, X is O, P is a hydrogen atom, R$^2$ is a hydrogen atom, G is O, R$^3$ and R$^4$ are phenyl groups, m is 3 and x is 1.

In a twelfth embodiment of the first embodiment, L is $(-CH_2-)_y$, D is O, T is $(-CH_2-)_x$, $R^1$ is a hydrogen atom, X is O, P is a hydrogen atom, $R^2$ is a hydrogen atom, G is O, $R^3$ and $R^4$ are phenyl groups, m is 2, x is 1 and y is an integer from 2 to about 6.

In a thirteenth embodiment of the twelfth embodiment, y is 2, 4 or 6.

In a fourteenth embodiment, the present invention pertains to a compound comprising a formula:

wherein L, T, $R^1$, X, $R^8$, $R^9$, P (with the provisio that P is absent when X is $NR^8R^9$), $R^2$, G, $R^3$, $R^4$, $R^{10}$, R, q, r, s, m, t, and x are as defined above.

In a fifteenth embodiment of the fourteenth embodiment L has a formula according to structure (I):

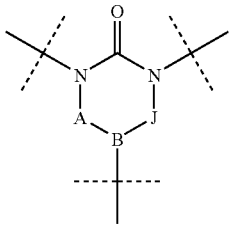

(I)

wherein A and J are each independently a hydrogen atom, an alkyl group, an aryl group, or together with B form a cyclic ring, provided when A and J are each independently a hydrogen atom, an alkyl group, or an aryl group then B is not present;

B is $NR^{11}$, O, or $(-CH_2-)_z$;

provided when A, B and J form a ring, then A and J are $(-CH_2-)_z$ or C=O;

$R^{11}$ is a hydrogen atom, an alkyl group, an aryl group or denotes a bond with T;

each z independently is an integer from 0 to 3; and provided when either A or J is C=O, then B is $NR^{11}$, O, or $(-CH_2-)_z$ and z must be at least 1.

In a sixteenth embodiment of either the fourteenth or fifteenth embodiments, T is $-CH_2-$.

In a seventeenth embodiment of any of the fourteenth through sixteenth embodiments, $R^1$ is a hydrogen atom.

In an eighteenth embodiment of any of the fourteenth through seventeenth embodiments, X is O and P is a hydrogen atom.

In a nineteenth embodiment of any of the fourteenth through eighteenth embodiments, $R^2$ is a hydrogen atom.

In a twentieth embodiment of any of the fourteenth through nineteenth embodiments, G is O.

In a twenty first embodiment of any of the fourteenth through twentieth embodiments, $R^3$ and $R^4$ are each individually aryl groups.

In a twenty second embodiment of any of the fourteenth through twenty first embodiments, m is 3.

In a twenty third embodiment of the fifteenth embodiment, A and J are both C=O and B is N.

In a twenty fourth embodiment of the fifteenth embodiment, A and J are both hydrogen atoms.

In a twenty fifth embodiment, the present invention pertains to a compound comprising a formula:

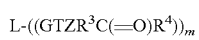

wherein Z is C=O, COO, or CONH when T $(-CH_2-)_x$; L, T, G, $R^3$, $R^4$, $R^{10}$, R, q, r, s, m, t, and x are as defined above.

In a twenty sixth embodiment of the twenty fifth embodiment, L has the formula according to structure (I):

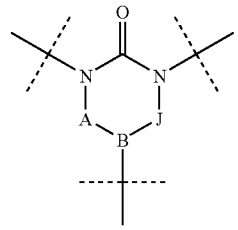

as defined above.

In a twenty seventh embodiment of either the twenty fifth or twenty sixth embodiments, T is $-CH_2-$.

In a twenty eighth embodiment of any of the twenty fifth through the twenty seventh embodiments, G is O.

In a twenty ninth embodiment of any of the twenty fifth through twenty eighth embodiments, $R^3$ and $R^4$ are each individually aryl groups.

In a thirtieth embodiment of any of the twenty fifth through twenty ninth embodiments, wherein m is 2.

In a thirty first embodiment of any of the twenty sixth through thirtieth embodiments, A and J are both C=O and B is $NR^{11}$.

In a thirty second embodiment of the twenty sixth embodiment, A and J are both hydrogen atoms.

In a thirty third embodiment of the twenty fifth embodiment, L has a formula according to structure (II):

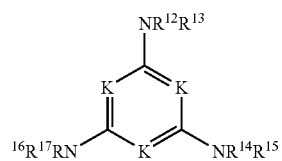

(II)

wherein $R^{12}$, $R^{13}$, $R^{14}$, $R^{15}$, $R^{16}$, $R^{17}$ are each independently a hydrogen atom, an alkyl or aryl group or denotes a bond with T, provided at least two of $R^{12}$, $R^{13}$, $R^{14}$, $R^{15}$, $R^{16}$, $R^{17}$ are bonded with T and each K, independently, is CH or N.

In a thirty fourth embodiment of the twenty fifth embodiment, L is C=O.

In a thirty fifth embodiment of the thirty fourth embodiment, G is NH.

In a thirty sixth embodiment of either the thirty fourth or thirty fifth embodiments, T is $-CH_2CH_2O-$.

In a thirty seventh embodiment of any of the thirty fourth through thirty sixth embodiments, Z is C=O.

In a thirty eighty embodiment of any of the thirty fourth through thirty seventh embodiments, $R^3$ is an aryl group.

In a thirty ninth embodiment of any of the thirty fourth through thirty eighth embodiments, $R^4$ is an aryl group.

In a fortieth embodiment, the present invention pertains to a compound comprising a formula:

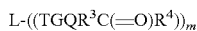

wherein L, T, G, $R^3$, $R^3$, $R^4$, $R^{10}$, R, q, r, s, m, t and x are as defined above and Q is $(-CH_2-)_p$, $(-CH_2CH_2-O-)_p$, ($-CH_2CH_2CH_2-O-$)$_p$ or ($-CH_2CH_2CH_2CH_2-O-$)$_p$ and p is an integer from 1 to about 10.

In a forty first embodiment of the fortieth embodiment, L has the formula according to structure (I):

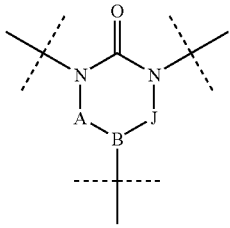

as defined above.

In a forty second embodiment if either the fortieth or forty first embodiments, T is $-CH_2-$.

In a forty third embodiment of any of the fortieth through forty second embodiments, G is O.

In a forty fourth embodiment of any of the fortieth through the forty third embodiment, $R^3$ and $R^4$ are each individually aryl groups.

In a forty fifth embodiment of any of the fortieth through forty fourth embodiments, m is 2.

In a forty sixth embodiment of any of the forty first through forty fifth embodiments, A and J are both C=O and B is $NR^{11}$.

In a forty seventh embodiment of any of the forty first through forty fifth embodiments, A and J are both hydrogen atoms.

In a forty eighth embodiment of the fortieth embodiment, L has the formula according to structure (II):

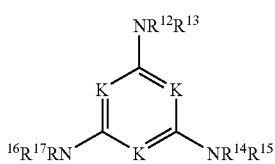

as described above.

In a forty ninth embodiment, the present invention pertains to a compound comprising a formula:

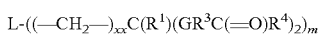

wherein L, $R^1$, G, $R^3$, $R^4$, $R^{10}$, R, q, r, s, m, t are as defined above and xx is an integer from 1 to about 10.

In a fiftieth embodiment of the forty ninth embodiment, L has the formula according to structure (I):

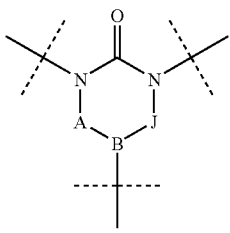

as defined above.

In a fifty first embodiment of the fiftieth embodiment, A and B are both hydrogen atoms.

In a fifty second embodiment of any of the forty ninth through fifty first embodiments, wherein xx is 1.

In a fifty third embodiment of any of the forty ninth through fifty second embodiment, wherein each $R^1$ is H.

In a fifty fourth embodiment of any of the forty ninth through fifty third embodiments, wherein each G is ($-CH_2-$)$_t$O— and t is 1.

In a fifty fifth embodiment of any of the forty ninth through fifty fourth embodiments, each $R^3$ and $R^4$ are each individually aryl groups.

In a fifty sixth embodiment of any of the forty ninth through fifty fifth embodiments, wherein xx is 1, each G is ($-CH_2-$)$_t$O— and t is 1, each $R^1$ is H and each $R^3$ and $R^4$ are each individually aryl groups.

In a fifty seventh embodiment, the present invention pertains to a compound comprising the formula:

wherein L, $R^1$, X, P, $R^8$, $R^9$, $R^2$, $R^{10}$, G, $R^3$, $R^4$, R, q, r, s, m and t are as defined as above.

In a fifty eighty embodiment of the fifty seventh embodiment, L is

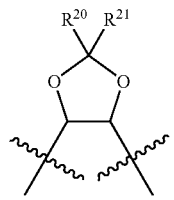

and $R^{20}$ and $R^{21}$ are each individually a hydrogen atom, an alkyl group or an aryl group.

In a fifty ninth embodiment of either the fifty seventh or fifty eighth embodiments, wherein $R^1$ is H.

In a sixtieth embodiment of any of the fifty seventh through fifty ninth embodiments, wherein X is O.

In a sixty first embodiment of any of the fifty seventh through sixtieth embodiments, P is H.

In a sixty second embodiment of any of the fifty seventh through sixty first embodiments, $R^2$ is H.

In a sixty third embodiment of any of the fifty seventh through sixty second embodiments, G is ($-CH_2-$)$_t$O— and t is 1.

In a sixty fourth embodiment of any of the fifty seventh through sixty third embodiments, $R^3$ and $R^4$ are each individually aryl groups.

In a sixty fifth embodiment of the fifty eight embodiment, $R^1$ is H, X is O, P is H, $R^2$ is H, G is ($-CH_2-$)$_t$O—, t is 1, $R^3$ and $R^4$ are each individually aryl groups and $R^{20}$ and $R^{21}$ are both methyl groups.

In a sixty sixth embodiment, the present invention pertains to a compound comprising the formula:

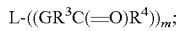

wherein L, G, $R^3$, $R^4$, $R^{10}$, R, q, r, s, m and t are as defined above.

In a sixty seventh embodiment, L is

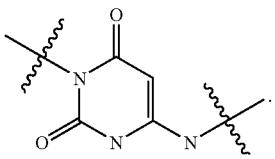

In a sixty eighty embodiment of either the sixty sixth or sixty seventh embodiments, G is C=O.

In a sixty ninth embodiment of any of sixty sixth through sixty eighth embodiments, $R^3$ and $R^4$ are each individually aryl groups.

In a seventieth embodiment of any of the sixty sixth through sixty ninth embodiments, G is C=O and $R^3$ and $R^4$ are each individually aryl groups.

In a seventy first embodiment of any of the first through seventieth embodiments, $R^3$ and $R^4$ are both phenyl groups and are tethered together via a CO, a S or a $CH_2$.

In a seventy second embodiment of any of the first through seventieth embodiments, $R^3$ and $R^4$ are both phenyl groups and include at least one $CH_3OCH_2CH_2O$—.

In a seventy third embodiment, the present invention pertains to a method to modify a substrate comprising the step of applying a compound of any of the first through seventy second embodiments to the surface of the substrate, such that the substrate surface is modified.

In a seventy fourth embodiment of the seventy third embodiment, the compound is photoactivated such that at least one photoactivatable group within the compound forms a covalent bond with the surface of the substrate.

In a seventy fifth embodiment of the seventy fourth embodiments, wherein the covalently bound compound is rephotoactivated in the presence of a target molecule, such that the target molecule is bound to the surface.

In a seventy sixth embodiment of the seventy third embodiment, wherein the compound and a target molecule are photoactivated simultaneously, such that the compound forms a covalent bond with the substrate surface and forms a bond with the target molecule.

In a seventy seventh embodiment, the present invention pertains to a composition comprising a polyvinylpyrrolidone and the compound of any of first through seventy second embodiments.

In a seventy eighty embodiment, the present invention provides a reaction product formed between a polyvinylpyrrolidone and the compound of any of the first through seventy second embodiments.

In a seventy ninth embodiments, the present invention pertains to a coating formed between a polyvinylpyrrolidone and the compound of any of the first through seventy second embodiments.

In an eightieth embodiment, the present invention pertains to a catheter coated with a coating formed from a polyvinylpyrrolidone and the compound of any of the first through seventy second embodiments.

In an eighty first embodiment, the present invention pertains to a method to prepare a coating, comprising the steps:

combining a polyvinylpyrrolidone and a compound of any of the first through seventy second embodiments, thereby forming a coating mixture; and subjecting the coating mixture to photoactivation.

In an eighty second embodiment, the present invention pertains to a method to modify a surface of a substrate, comprising the steps:

combining a polyvinylpyrrolidone and a compound of any of the first through seventy second embodiments, thereby forming a coating mixture;

coating the surface of the substrate with the coating mixture; and subjecting the coating mixture to photoactivation.

In an eighty third embodiment, the present invention pertains to a method to modify a surface of a catheter, comprising the steps:

combining a polyvinylpyrrolidone and a compound of any of the first through seventy second embodiments, thereby forming a coating mixture;

coating the surface of the catheter with the coating mixture; and subjecting the coating mixture to photoactivation.

In an eighty fourth embodiment, and in particular, with respect to the fourteenth embodiment, the linker can be $(-OCH_2CH_2O-)_{qq}$, $(-OCH_2CH_2CH_2O-)_{qq}$, $(-O-(CH_2)_{ii}-O-)_{qq}$ or $(-O(CH_2)_{ii}-O-(CH_2)_{jj}-O-)_{qq}$, wherein qq is an integer from 1 and about 500, ii is an integer from 1 and about 500 and jj is an integer from 1 and about 500. For example, when $(-OCH_2CH_2O-)_{qq}$ is a linker, qq can be 2, 4 or 6, thus producing linkages having diethylene, tetraethylene and hexaethylene glycol type moieties as in Examples 14, 22 and 24 described below.

In an eighty fifth embodiment of the eighty fourth embodiment, L is $(-OCH_2CH_2O-)_{qq}$, T is $(-CH_2-)_x$, $R^1$, X, $R^8$, $R^9$, P (with the provisio that P is absent when X is $NR^8R^9$), $R^2$, G, $R^3$, $R^4$, $R^{10}$, R, q, r, s, m, t, qq, ii, jj and x are as defined above.

In an eighty sixth embodiment of the eighty fifth embodiment, qq is an integer from 1 to 10, i.e., 2, 4 or 6, x is an integer from 1 to 10, i.e., 1, m is 2, $R^1$ is H, X is O, P is H, G is O and $R^3$ and $R^4$ are aryl groups, i.e., phenyl groups.

In an eighty seventh embodiment, the eighty fourth through eighty sixth embodiments are applicable to the seventy third through eighty third embodiments, substituting for the first through seventy second embodiments where appropriate.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLE 1

Synthesis of Trifunctional Triazine Crosslinker 1.2 g (4 mmol) of triglycidyl isocyanurate (Aldrich Chemicals, Milwaukee, Wis.) and 2.4 g (12 mmol) of 4-hydroxybenzophenone (Aldrich Chemicals, Milwaukee, Wis.) were mixed in a 50-ml round bottom flask containing a magnetic stir bar. The flask was flushed with argon for 10 min and heated to 130° C. in an oil bath. Once the reaction mixture melted, 6 mg (0.02 mmol) of triphenylphosphine (Aldrich Chemicals, Milwaukee, Wis.) was added. The mixture was stirred for another 2 minutes under argon and cooled to room temperature. The reaction residue was dissolved in 30 ml chloroform, then washed with 4N NaOH (30 ml×3) and deionized water (30 ml×3). The organic layer was dried over magnesium sulfate and concentrated to dryness on the under reduced pressure. The product was purified by column chromatography (silica gel, 230-400 mesh, Whatman, Inc.) using ethyl acetate as eluent ($R_f$~4.5). The fractions containing the pure product were combined and concentrated under reduced pressure and a white powder was obtained after drying under vacuum (yield 70%).

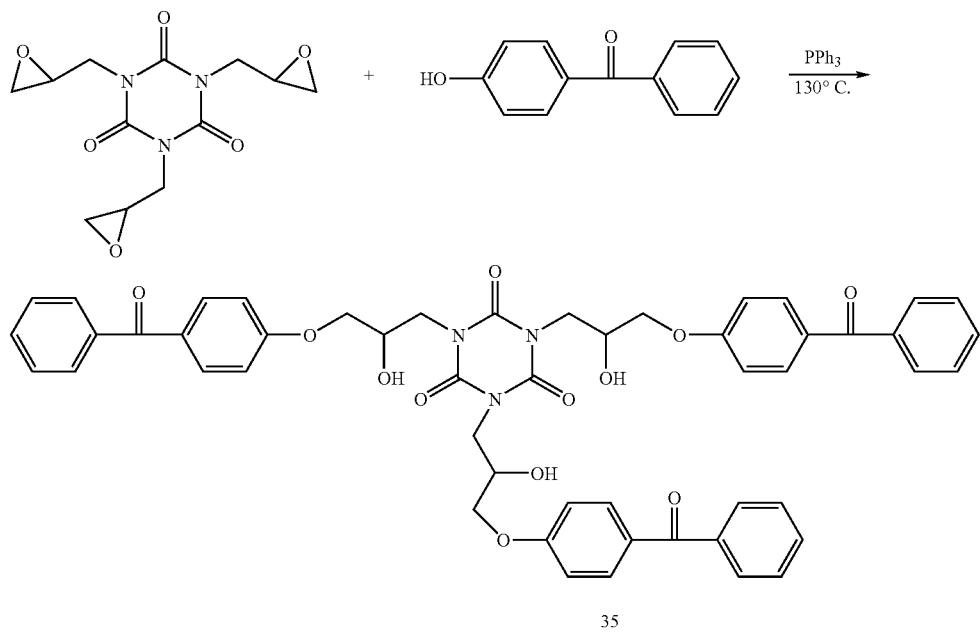

The crosslinker is soluble in most common solvents including chloroform, methylene chloride, acetone, ethyl acetate, isopropanol, etc. $^1$H NMR (CDCl$_3$) confirmed the structure of the product. The peaks at d 7.78 ppm (m, 12H), 7.46 ppm (m, 9H), 6.98 ppm (m, 6H) were the typical signals from 4-subsituted benzophenone. The peak at d 4.35 ppm (m, 6H) was assigned to the protons of methylene connected to phenoxy group. The peak at d 4.13 ppm (m, 9H) was a combination of 6 protons of 3 methylene groups connected to nitrogen atom and 3 protons from 3 methine groups. The peak at d 3.00 ppm (s, 3H) corresponded to hydroxyl groups.

EXAMPLE 2

Application of Triazine Crosslinker to Create a Photoreactive Surface

A photoreactive poly(ε-caprolactone) (PCL) film was prepared by incorporating the crosslinker in a film casting polymer solution. A solution containing 20 mg/ml PCL (Aldrich Chemicals, Milwaukee, Wis.) and 0.4 mg/ml triazine crosslinker (as prepared in Example 1) was cast onto a glass slide. 10 μl of 50 mg/ml poly(vinylpyrrolidone) (PVP), 30K, Kollidon K30 BASF, NJ) in isopropanol solution was added onto the film. After complete evaporation of the isopropanol, the film was illuminated under UV for 20 minutes (UV Crosslinker, UVP CL-1000, Upland, Calif., 254 nm light, 120,000 μJ/cm$^2$). The coated film was incubated in deionized water on a shaker for 3 hours to remove unbound PVP. A homogeneous PVP coating could be seen on the PCL film by staining with a solution of Congo Red (0.5% w/v aqueous solution) indicating a uniform distribution of crosslinker on the film surface. A PCL film without triazine crosslinker added showed no staining, indicating all unbound PVP was removed by the rinse.

EXAMPLE 3

Synthesis of Photoreactive Glycol Crosslinker 2.26 g 4-hydroxybenzophenone (Aldrich Chemicals, Milwaukee, Wis.) was dissolved in 50 ml of acetone, and 0.532 ml of glycerol triglycidyl ether (Polysciences, Warrington, Pa.), and 3.3 g potassium carbonate (Aldrich Chemicals, Milwaukee, Wis.) were added to the solution. The reaction mixture was heated to reflux over 24 hours. After 24 hours of heating, thin layer chromatography (TLC) showed consumption of the glycerol starting material (eluent 20:1 Chloroform: methanol) and the emergence of three uv active spots. The acetone was removed by rotary evaporation and the residue was dissolved in chloroform, and filtered. The resulting chloroform solution was washed three times with 4N NaOH aqueous solution, once with deionized water, then twice with 1N HCl aqueous solution, and three times again with deionized water. The chloroform solution was dried over magnesium sulfate, filtered, and the solvent removed by rotary evaporation. The resulting oil was washed three times with diethyl ether and dried. This treatment removed all 4-hydroxybenzophenone starting material, with TLC revealing the same three uv active spots. These three products presumably correspond to single, double, and triple substitution of benzophenone on the glycerol compound.

EXAMPLE 4

Wettable Coatings with Glycol Linker

A coating solution was made up from the crude glycol linker product isolated in Example 3 (0.5 mg/ml glycol in isopropanol with 50 mg/ml polyvinylpyrrolidone (Kollidon K30, BASF, NJ)). 100 µl of the coating solution was applied to PVC coverslips (Fisher Scientific, Pittsburgh, Pa.) and allowed to dry overnight. All pieces were illuminated for a set time in a uv crosslinker (UVP CL-1000, Upland, Calif., 254 nm light, 120,000 µJ/cm$^2$) from 0 to 10 minutes. Pieces were then rinsed for 30 minutes in deionized water with gentle agitation. The static contact angle with water was taken on a goniometer (MicroVu 400, Santa Ana, Calif.), three 3 µl drops of water were measured, three times apiece. Contact angles are shown below.

| Sample illumination time | Contact Angle |
| --- | --- |
| 0 minutes | 38.1 ± 10.0 |
| 0.5 minutes | 28.4 ± 7.8 |
| 1 minute | 31.7 ± 6.3 |
| 2 minutes | 31.1 ± 4.4 |
| 5 minutes | 23.1 ± 8.8 |
| 10 minutes | 29.1 ± 3.0 |
| Uncoated | 61.9 ± 1.4 |

EXAMPLE 5

Higher Concentration Coating with Glycol Crosslinker

A coating solution was made up from the crude glycol linker product isolated in Example 3 (2.0 mg/ml glycol in 90:10 isopropanol:acetone with 50 mg/ml polyvinylpyrrolidone (Kollidon K30, BASF, NJ)). 500 µl of the coating solution was applied to PVC coverslips (Fisher Scientific, Pittsburgh, Pa.) and allowed to dry overnight. Sample pieces were illuminated for 0, 1, 2, or 5 minutes in a uv crosslinker (UVP CL-1000, Upland, Calif., 254 nm light, 120,000 µJ/cm$^2$). Pieces were then rinsed for 30 minutes in deionized water with gentle agitation. After rinsing the pieces were stained with a solution of 3.5 mg/ml Congo Red dye in deionized water, by dipping in the solution for 30 seconds, then rinsing in deionized water. Congo Red stains the PVP giving evidence of coated samples. Pieces illuminated for five minutes showed bright red stains, indicating PVP, while 0,1, and 2 minutes showed little or no red color.

EXAMPLE 6

Coating with Triazine Crosslinker

A coating solution of purified triazine crosslinker isolated in Example 1 was made by adding 44 mg of crosslinker to 1 ml of acetone, diluted with 19 ml of isopropanol, then adding 1000 mg of poly(vinylpyrrolidone) (PVP) (Kollidon K30, BASF, NJ). The resulting solution was thoroughly mixed on an orbital shaker for four hours. 18 samples were prepared by adding 100, 200, or 500 µl of coating solution onto PVC Coverslips (Fisher Scientific, Pittsburgh, Pa.) (n=6 for each condition), then air drying. The sample pieces were illuminated for five minutes in a uv chamber (UVP CL-1000, Upland, Calif., 254 nm light, 120,000 µJ/cm$^2$), then rinsed for four hours in deionized water with gentle agitation. 4 pieces of each variable were then stained with Congo red dye to determine the presence of PVP. For each coating condition, two of the four stained pieces were then rubbed with a wet glove to determine durability of the coating to simple rubbing. The results are shown in the following table. The remaining two unstained sample pieces for each coating condition were then assessed for static contact angle by threefold measurement of three 3 µl drops of water on a goniometer (MicroVu 400, Santa Ana, Calif.). Results, included in the following table, show that after rinsing the top monolayer of each surface is hydrophilic and presumably contains PVP.

| Coating | Congo Red stain indicating PVP | Congo red stain after rubbing | Contact angle (rinse only) |
| --- | --- | --- | --- |
| 100 ml | ++ | ++ | 35.3 ± 3.4 |
| 200 ml | ++ | ++ | 38.7 ± 2.6 |
| 500 ml | +− | −− | 29.2 ± 2.2 |

EXAMPLE 7

Coating Catheters with Triazine Crosslinker

Three coating solutions were made, each with 12 mg linker (example 1), 3 ml of isopropanol and 3 ml of 100 mg/ml polymer solution in isopropanol where the polymer solutions were composed of K30 (polyvinylpyrrolidone MW ~30,000, Kollidon 30 BASF), K90 (polyvinylpyrrolidone MW ~90,000, Kollidon 90 BASF) and 1:1 K30:K90. The coating solutions were sonicated. 18 1 inch sections of silicone rubber commercial catheters were cleaned with isopropanol, then hand dipped into the coating solutions (n=6) and withdrawn slowly. They were placed upright to dry and half were then illuminated for 10 minutes in a uv chamber (UVP CL-1000, Upland, Calif., 254 nm light, 120,000 µJ/cm$^2$). All sample pieces were rinsed for 30 minutes in deionized water, then stained with Congo Red to detect the presence of PVP. All illuminated sample pieces showed bright red stain indicating significant PVP, while none of the non-illuminated samples showed staining. There were no significant other differences between the three coatings.

EXAMPLE 8

Lubricity Formulation for Long Dry Time

A solution of 37.0 mg triazine tribenzophenone from Example 1 in 66.6 ml of 50 mg/ml polyvinylpyrrolidone (PVP, K90 from BASF Corp., Florham Park, N.J.) in isopropanol (Fisher Scientific, Pittsburgh, Pa.) was diluted with 7.4 ml of 50 mg/ml polyvinylpyrrolidone (K30, from BASF Corp., Florham Park, N.J.) in isopropanol. This solution was stirred at 45° C. for 1 hour to allow thorough mixing. 9 inch pieces of PVC tubing (Hollister, Libertyville, Ill.) were coated with the solution by immersing the pieces in the solution for 30 seconds, then extracting at 0.5 cm/sec. Pieces were prepared for coating by cleaning with a brief isopropanol rub. The total coated length was 6 inches. A polyethylene mandrel was inserted in the lumen for ease of coating (0.115 inch diameter HDPE, Small Parts, Inc. Logansport, Ind.) The pieces were air dried at room temperature for 3 minutes, then irradiated with ultraviolet light (300 to 400 nm) for 3 minutes (Harland Medical UVM400, Eden Prairie, Minn.). The pieces were tested with a commercial friction tester (Harland Medical, FTS 5000, Eden Prairie, Minn.) for lubricity and dry time.

In a lubricity test, the pieces were hydrated for 2 minutes with water, then silicone pads compressed the tubing while immersed in water as the tubing was pulled upward at 1.0 cm/sec for 6.0 cm. The clamps were then released and the tubing moved freely downward 6.0 cm at 2.0 cm/sec. This cycle was repeated fifteen times. The average friction force required to pull the coated tubing through the silicone pads with 300 g of force on them was 5.6 g. The average friction force to pull uncoated tubing through the silicone pads exceeds 250 g. No significant change was seen in the friction test throughout the fifteen cycles.

In a dry test, the pieces were hydrated for 2 minutes with water, followed by 4 minutes of air drying at room temperature. The friction test above was repeated without any water present, simply rubbing the coating in air. The test ran for 50 cycles rather than 15. The return velocity was 5.0 cm/sec instead of 2.0 cm/sec. During this time the average lubricity decreased from 5.6 g to 6.6 g; the coating maintained its integrity and felt wet to the touch. The entire test lasted over 22 minutes including the 4 minutes of dry time prior to rubbing. A commercial hydrophilic catheter was compared as a control. The average friction force on a Mentor Self-cath Plus (Mentor, Minneapolis, Minn.) increased from 11.6 g to over 50 g in 10 cycles in less than 8 minutes of total drying time. At this point the coating felt dry to the touch.

EXAMPLE 9

Lubricity on a Catheter

The coating solution from Example 8 was used to coat 6 inches of an uncoated Mentor commercial catheter (Mentor Self-cath, Minneapolis, Minn.) following the procedure in Example 1. The catheters were prepared by snipping off the end with outlets, then cleaning with an isopropanol wipe. After air drying, the catheters were dipped in the coating solution where they remained for 30 seconds, followed by extraction at 0.5 cm/sec. The coatings dried for 3 minutes, then were irradiated for 3 minutes with ultraviolet light at 300 to 400 nm (Harland Medical UVM400, Eden Prairie, Minn.). No mandrel was used for the coating.

Friction testing for lubricity followed the protocol described in Example 8. Lubricity on the coated catheter averaged 11.9 g. It showed no significant changes in the fifteen cycles.

Dry time was tested following the protocol in Example 8. The dry time friction increased from an average of 12.6 g per cycle to 38.5 g per cycle (cycle 50). The peak friction increased from 18.3 g to 280.2 g in a dramatic rise beginning in cycle 44. The coating remained wet to the touch. As described in Example 8, the coated Mentor catheter (Self-cath Plus, Mentor, Minneapolis, Minn.) increased friction in just 10 cycles.

EXAMPLE 10

Lubricity on Polyethylene Rod

A coating solution was made up of 1.0 mg/ml triazine crosslinker (Example 1), 50 mg/ml polyvinylpyrrolidone where 75% v/v is high molecular weight (BASF K90 90,000 MW, BASF Corp. Florham Park, N.J.) and 25% v/v is low molecular weight (BASF K30, 30,000 MW, BASF Corp. Florham Park, N.J.) in isopropanol. High density polyethylene rod (0.115 inch diameter, Small Parts Inc, Logansport, Ind.) was cleaned with isopropanol, air dried and coated. The pieces were coated on a Harland Medical PCX (Harland Medical, Eden Prairie, Minn.) with 9 inches coated distance, 30 seconds dwell in solution, 0.5 cm/sec extraction speed, 2 minutes dry, then were irradiated for 3 minutes with ultraviolet light at 300 to 400 nm) (Harland Medical UVM400, Eden Prairie, Minn.).

Lubricity tests on the coated rod were performed on the Harland Medical FTS5000. Pieces were compressed between silicone pads with 500 g force while immersed in water, then pulled through the pads at 1.0 cm/sec for 6.0 cm. The clamps then released and the pieces were moved downward at 2.0 cm/sec. Eleven cycles were completed, with an average friction force of 3.9 g and a peak friction force of 6.7 g.

EXAMPLE 11

Lubricity on Catheter

A 6 inch segment of a Mentor Self-Cath catheter (Mentor, Minneapolis, Minn.) was coated with a solution of 0.5 mg/ml triazine crosslinker (Example 1) and 50 mg/ml PVP where 75% v/v is high molecular weight (BASF K90 90,000 MW, BASF Corp. Florham Park, N.J.) and 25% v/v is low molecular weight (BASF K30, 30,000 MW, BASF Corp. Florham Park, N.J.) in isopropanol. The catheters were prepared by snipping off the end with outlets, then cleaning with an isopropanol wipe. After air drying, the catheters were dipped in the coating solution where they remained for 30 seconds, followed by extraction at 0.5 cm/sec. The coatings dried for 3 minutes, then were irradiated for 3 minutes with ultraviolet light at 300 to 400 nm) (Harland Medical UVM400, Eden Prairie, Minn.). No mandrel was used for the coating.

The lubricity was tested on a Harland Medical FTS5000 (Harland Medical, Eden Prairie, Minn.) with 300 g of clamp force on silicone pads over 6 cm of coated tubing as described in Example 8. The coated catheter was hydrated for 2 minutes prior to the test. The average friction force was 11.4 g with a peak friction force of 26.2 g.

Drying times were tested according to the protocol in Example 8. Lubricity decreased from an average frictional force of 11.4 g in cycle 1 to 121.8 g in cycle 18 to over 250 g in cycle 22. Lubricity was relatively constant until a force increase at approximately cycle 15.

EXAMPLE 12

Lubricity on a Catheter 6 inch segments of PVC tubing supplied by Hollister (Libertyville, Ill.) were coated with a solution of 0.5 mg/ml triazine crosslinker (Example 1) and 50 mg/ml PVP where 80% v/v is high molecular weight (BASF K90 90,000 MW, BASF Corp. Florham Park, N.J.) and 20% v/v is low molecular weight (BASF K30, 30,000 MW, BASF Corp. Florham Park, N.J.) in isopropanol. The pieces were immersed in the solution for 30 seconds, then extracting at 0.5 cm/sec. Pieces were prepared for coating by cleaning with a brief isopropanol rub. A polyethylene mandrel was inserted in the lumen for ease of coating (0.115 inch diameter HDPE, Small Parts, Inc. Logansport, Ind.) The pieces were air dried at room temperature for 3 minutes, then irradiated with ultraviolet light for 3 minutes at 300-400 nm (Harland Medical UVM400, Eden Prairie, Minn.). The pieces were tested with a commercial friction tester (Harland Medical, FTS 5000, Eden Prairie, Minn.) for lubricity and dry time.

The lubricity test followed the protocol in Example 8. Average frictional force on the coated pieces was 5.7 g over fifteen cycles, with average peak force of 8.4 g. Coatings were slick to the touch.

Dry Time tests followed the protocol in Example 8. Average frictional forces increased from 5.2 g (cycle 15) to 75.6 g (cycle 36) to 215.6 (cycle 50). Lubricity was relatively constant between cycle 1 and cycle 34. The total dry time is over 22 minutes; dry time to cycle 34 is over 14 minutes.

EXAMPLE 13

Lubricity on a Catheter 9 inch segments of a Mentor Self-Cath catheter (Mentor, Minneapolis, Minn.) was coated with a solution of 0.5 mg/ml triazine crosslinker (Example 1) and 50 mg/ml PVP where 70% v/v is high molecular weight (BASF K90 90,000 MW, BASF Corp. Florham Park, N.J.) and 30% v/v is low molecular weight (BASF K30, 30,000 MW, BASF Corp. Florham Park, N.J.) in isopropanol. The pieces were immersed in the solution for 30 seconds, then extracting at 0.5 cm/sec. Pieces were prepared for coating by cleaning with a brief isopropanol rub. A polyethylene mandrel was inserted in the lumen for ease of coating (0.115 inch diameter HDPE, Small Parts, Inc. Logansport, Ind.) The pieces were air dried at room temperature for 3 minutes, then irradiated with ultraviolet light for 3 minutes (Harland Medical UVM400, Eden Prairie, Minn.). The pieces were tested with a commercial friction tester (Harland Medical, FTS 5000, Eden Prairie, Minn.) for lubricity.

The lubricity test followed the protocol in Example 8. No mandrel was used in the lubricity testing. Average frictional force on the coated pieces was 16.2 g over nine cycles, with average peak force of 19.3 g. Coatings were slick to the touch.

EXAMPLE 14

Diethylene Glycol Photocrosslinker Synthesis

4-Hydroxybenzophenone, 2.2758 g (11.4811 mMol, 2 mol eq, Alfa Aesar, Ward Hill, Mass.), was added to a 100 mL round bottom flask equipped with a reflux condenser and dissolved in 75 mL of acetone. Ethylene glycol diglycidyl ether, 1.0000 g (5.7405 mMol, 1 mol eq Aldrich Chemicals, Milwaukee, Wis.) followed by potassium carbonate, 3.1736 g (22.9621 mMol, 4 mol eq), was then added to the mixture and was heated at reflux overnight. After cooling, the remaining solid was filtered and organic layer was removed in vacuo. The crude product mixture was redissolved in 60 mL of chloroform and the residual 4-Hydroxybenzophenone was removed by washing with a 4N NaOH aqueous solution. The organic layer was then dried over $MgSO_4$ and filtered to remove drying agent. A portion of the chloroform solvent was removed in vacuo until 5 mL remained. The product was isolated by silica column (EMD Silica Gel 0.040-0.063 mm, 230-400 mesh, 60 Å) using (9:1) Ethyl Acetate:Hexane as eluent. Elution was monitored by TLC. $R_f$ value of desired product was 0.40 in same eluent. $^1$H NMR ($CDCl_3$): δ=7.7-7.9, 7.4-7.6, 6.9-7.1 (m, characteristic of benzophenone), 4.2-4.3 (m), 4.0-4.2 (m), 3.6-3.8 ppm (m).

EXAMPLE 15

Coating with Diethylene Glycol Photocrosslinker

The coating solutions consisted of 2 mg/mL crosslinker, 1 mg/mL crosslinker and 0.5 mg/mL crosslinker where the crosslinker was either the tri-isocyanurate synthesized in Example 1, or the di-ethylene glycol synthesized in Example 14. All coating solutions contained 50 mg/mL polyvinylpyrrolidone (Kollidon 90, BASF#5000784, Florham Park, N.J.) in isopropanol (Fisher Scientific A416-4, Pittsburgh, Pa.). The solutions were then incubated overnight at 60° C. to incorporate all the ingredients into solution. PVC coverslips (Fisher Scientific, Pittsburgh, Pa.) were cleaned with isopropanol. 100 uL of the coating solutions were then deposited onto the surface of the coverslips and allowed to dry. After drying the coated samples were split into two sets: one to be illuminated and the other not. The illuminated samples were then placed under a UV lamp (Harland Medical UVM400, Eden Prairie, Minn.) for 5 minutes. The lamp was set to be 4 inches from the surface of the coverslips. After illumination all samples were then washed in deionized water for 5 minutes on a rotary shaker. The samples were then divided once more into rubbed and unrubbed sets. The rubbed set was rubbed between gloved fingers to determine durability. The samples were then rinsed with deionized water and stained with the Congo Red Solution (3.5 mg/mL Congo Red (Sigma#860956, St. Louis, Mo.) in deionized water).

| | Results | | | |
|---|---|---|---|---|
| | Un-illuminated Rubbed | Unrubbed | Illuminated Rubbed | Unrubbed |
| di-ethylene glycol[Conc.] | | | | |
| .5 mg/mL | [−] | [−] | [+] | [+] |
| 1 mg/mL | [−] | [−] | [++] | [++] |
| 2 mg/mL | [−] | [−] | [+++] | [+++] |
| Tri-isocyanurate[Conc.] | | | | |
| .5 mg/mL | [−] | [−] | [+++] | [+++] |
| 1 mg/mL | [−] | [−] | [+++] | [+++] |
| 2 mg/mL | [−] | [−] | [++] | [++] |

EXAMPLE 16

Synthesis of Urea Photo-Crosslinker

Bis-2,3-dihydroxypropylurea, 0.3000 g (1.4408 mMol, 1 mol equiv. Aldrich Chemicals, Milwaukee, Wis.), was added to a 50 mL round bottom flask under argon sweep and dissolved in 20 mL of DMF (Fisher Scientific, Pittsburgh, Pa.). Sodium hydride (60% dispersion in mineral oil, Aldrich Chemicals, Milwaukee, Wis.), 0.2305 g (5.7633 mMol, 4 mol eq), was then added and stirred at room temperature for 20 minutes. 4-(Bromomethyl)benzophenone, 1.5858 g (5.7633 mMol, 4 mol equiv. Aldrich Chemicals, Milwaukee, Wis.), was added to the mixture and heated at reflux under positive argon pressure for five hours. After cooling, the reaction mixture was dissolved in 200 mL of deionized water and the crude product was extracted with chloroform. The organic layer was then dried over magnesium sulfate and filtered to remove the drying agent. The chloroform was removed in vacuo and the crude product was redissolved in a minimal amount of (85:15) $CHCl_3$:MeOH. The product was isolated by silica gel column (EMD Silica Gel 0.040-0.063 mm, 230-400 mesh, 60 Å) using (85:15) $CHCl_3$:MeOH as eluent. Elution was monitored by TLC. $R_f$ value of desired product was 0.74 in the same eluent. Several spots were isolated together and may represent two, three, and four functionalized crosslinkers. $^1$H NMR (CDCl$_3$): δ=7.3-7.9 (m, characteristic benzophenone pattern), 4.5-4.7 (m), 3.5-3.8 ppm (m).

EXAMPLE 17

Coating with Urea Photo-Crosslinker

The coating solutions consisted of 2 mg/mL crosslinker, 1 mg/mL crosslinker and 0.5 mg/mL crosslinker where the crosslinker was the photo-urea synthesized in Example 16. All coating solutions contained 50 mg/mL polyvinylpyrrolidone (Kollidon 90, BASF#5000784, Florham Park, N.J.) in isopropanol (Fisher Scientific A416-4, Pittsburgh, Pa.). The solutions were then incubated overnight at 60° C. to incorporate all the ingredients into solution. PVC coverslips (Fisher Scientific, Pittsburgh, Pa.) were cleaned with isopropanol. 100 uL of the coating solutions were then deposited onto the surface of the coverslips and allowed to dry. After drying the coated samples were split into two sets: one to be illuminated and the other not. The illuminated samples were then placed under a UV lamp (Harland Medical UVM400, Eden Prairie, Minn.) for 5 minutes. The lamp was set to be 4 inches from the surface of the coverslips. After illumination all samples were then washed in deionized water for minutes on a rotary shaker. The samples were then divided once more into rubbed and unrubbed sets. The rubbed set was then rubbed between gloved fingers to determine durability. The samples were then rinsed with deionized water and stained with the Congo Red Solution (3.5 mg/mL Congo Red (Sigma#860956, St. Louis, Mo.) in deionized water).

| | Results | | | |
|---|---|---|---|---|
| | Unilluminated | | Illuminated | |
| Urea[Conc.] | Rubbed | Unrubbed | Rubbed | Unrubbed |
| .5 mg/mL | [−] | [−] | [+++] | [+++] |
| 1 mg/mL | [−] | [−] | [++] | [+++] |
| 2 mg/mL | [−] | [−] | [++] | [+++] |

EXAMPLE 18

Synthesis of Polyalcohol Photo-Crosslinker 3,4-O-Isopropylidene-D-mannitol, 0.5000 g (2.2498 mMol, 1 mol eq, Aldrich Chemicals, Milwaukee, Wis.), was added to a 50 mL round bottom flask equipped with a reflux condenser and dissolved in 25 mL of chloroform under argon sweep. NaH (with 60% dispersion in mineral oil, Aldrich Chemicals, Milwaukee, Wis.), 0.2700 g (6.7495 mMol, 3 mol eq), was added and then stirred for 30 minutes. 4-(Bromomethyl)benzophenone (Aldrich Chemicals, Milwaukee, Wis.), 0.1.23808 g (4.4996 mMol, 2 mol eq), was added to the mixture and heated at reflux overnight under positive argon pressure. After cooling, the organic layer was filtered to remove precipitate. A portion of the chloroform solvent was removed in vacuo until 5 mL remained. The product was isolated by silica gel column (EMD Silica Gel 0.040-0.063 mm, 230-400 mesh, 60 Å) using chloroform as eluent. Elution was monitored by TLC. R$_f$ value of desired product was 0.40 in the same eluent. Three compounds were isolated and may represent different isomers of the compound. $^1$H NMR (CDCl$_3$): δ=7.3-7.9 (m, characteristic of benzophenone pattern), 4.6-5.0 (dd), 4.5-4.6 (s), 3.6-3.9 (m), 1.5-1.6 ppm (s).

EXAMPLE 19

Coating with Polyalcohol Photo-Crosslinker

The coating solutions consisted of 2 mg/mL, 1 mg/mL, or 0.5 mg/mL polyalcohol crosslinker from Example 18, with all solutions containing 50 mg/mL polyvinylpyrrolidone (Kollidon 90, BASF#5000784, Florham Park, N.J.) in chloroform (Fisher Scientific, Pittsburgh, Pa.). The three solutions were shaken until completely dissolved in solution. High density polyethylene rod (Small Parts Inc, Logansport, Ind.) was then cleaned with isopropanol, then dipped into the previously made coating solutions and extracted at a speed of 0.5 cm/sec. After drying the coated samples were split into two sets: one to be illuminated and the other not. The illuminated samples were then placed under a UV lamp (Harland Medical UVM400, Eden Prairie, Minn.) for 5 minutes at a distance of 4 inches from the lamp. After illumination all samples were then washed with deionized water for 5 minutes on a rotary shaker. The samples were then divided once more into rubbed and unrubbed sets. The rubbed set was then rubbed between gloved fingers to determine durability. The samples were then rinsed with deionized water and stained with the Congo Red Solution (3.5 mg/mL Congo Red (Sigma#860956, St. Louis, Mo.) in deionized water).

| polyalcohol [Conc.] | Unilluminated | | Illuminated | |
|---|---|---|---|---|
| | Rubbed | Unrubbed | Rubbed | Unrubbed |
| .5 mg/mL | [−] | [−] | [+] | [+++] |
| 1 mg/mL | [−] | [−] | [++] | [+++] |
| 2 mg/mL | [−] | [−] | [+++] | [+++] |

EXAMPLE 20

Synthesis of Photo-Uracil Crosslinker

6-Aminouracil, 0.1091 g (0.8581 mMol, 1 mol eq, Aldrich Chemicals, Milwaukee, Wis.), was added to a 100 mL round bottom flask equipped with a reflux condenser and dissolved in 50 mL of chloroform under argon sweep. 4-(Benzoyl) benzoic acid chloride, 0.4199 g (1.7161 mMol, 2 mol eq, Aldrich Chemicals, Milwaukee, Wis.), 4-Dimethylaminopyridine, 0.01260 g (3-5 wt % of 4-(Benzoyl)benzoic acid chloride, Aldrich Chemicals, Milwaukee, Wis.), and Triethylamine, 0.1042 g (1.02969 mMol, 1.2 mol eq, Aldrich Chemicals, Milwaukee, Wis.) were heated at reflux under positive argon pressure overnight. After cooling, the reaction mixture was filtered to remove precipitate. The organic layer was removed in vacuo and the remaining crude reaction mixture was redissolved in a minimal amount of (9:1) CHCl$_3$:MeOH. The desired product was isolated by silica gel column (EMD Silica Gel 0.040-0.063 mm, 230-400 mesh, 60 Å) using the (9:1) CHCl$_3$:MeOH as eluent. Monitor elution by TLC. R$_f$ value of desired product was 0.56 in the same eluent.

EXAMPLE 21

Coating of Photo-Uracil Crosslinker

The coating solutions consisted of 2 mg/mL, 1 mg/mL, or 0.5 mg/mL photouracil crosslinker from Example 20, with all solutions containing 50 mg/mL polyvinylpyrrolidone (Kollidon 90, BASF#5000784, Florham Park, N.J.) in chloroform (Fisher Scientific, Pittsburgh, Pa.). The three solutions were shaken until completely dissolved in solution. High density polyethylene rod (Small Parts Inc, Logansport, Ind.) was then cleaned with isopropanol, then dipped into the previously made coating solutions and extracted at a speed of 0.5 cm/sec. After drying the coated samples were split into two sets: one to be illuminated and the other not. The illuminated samples were then placed under a UV lamp (Harland Medical UVM400, Eden Prairie, Minn.) for 5 minutes at a distance of 4 inches from the lamp. After illumination all samples were then washed with deionized water for 5 minutes on a rotary shaker. The samples were then divided once more into rubbed and unrubbed sets. The rubbed set was then rubbed between gloved fingers to determine durability. The samples were then rinsed with deionized water and stained with the Congo Red Solution (3.5 mg/mL Congo Red (Sigma#860956, St. Louis, Mo.) in deionized water).

| uracil [Conc.] | Unilluminated Rubbed | Unrubbed | Illuminated Rubbed | Unrubbed |
|---|---|---|---|---|
| .5 mg/mL | [−] | [−] | [++] | [+++] |
| 1 mg/mL | [−] | [−] | [+++] | [+++] |
| 2 mg/mL | [−] | [−] | [+++] | [+++] |

EXAMPLE 22

Synthesis of TEG Photo-Crosslinker 1.94 g of tetraethylene glycol (Aldrich Chemicals, Milwaukee, Wis.) was dried under vacuum at 50° C. for 2 h and dissolved in 50 ml anhydrous tetrahydrofuran. 6.8 g of 4-(bromomethyl)benzophenone (Aldrich Chemicals, Milwaukee, Wis.) and 1.8 g sodium hydride (60% in mineral oil, Aldrich Chemicals, Milwaukee, Wis.) were added to the solution. The mixture was stirred overnight under refluxing condition and argon protection. The reaction solution was cooled to room temperature and filtered. The filtrate was concentrated by rotary evaporation and the residue was purified on column chromatography (silica gel, 230-400 mesh, Whatman, Inc.) using 25:1 chloroform/methanol mixture as eluent. The fractions containing the pure product were combined and concentrated to dryness by rotary evaporation to yield yellowish oil (yield 80%).

The TEG crosslinker is soluble in most common solvents including chloroform, methylene chloride, tetrahydrofuran, acetone, ethyl acetate, isopropanol, etc. $^1$H NMR (CDCl$_3$) confirmed the structure of the product. The peaks at 7.49~7.79 ppm (m, 18H) were the typical signals from 4-subsituted benzophenone. The peak at 4.66 ppm (s, 4H) was assigned to the protons of methylene connected to benzophenone group. The peak at 3.70 ppm (m, 16H) corresponded to ethylene groups.

EXAMPLE 23

Coating with TEG Photo-Crosslinker

A coating solution was made by dissolving 0.5 g of poly (vinylpyrrolidone) (PVP) (Kollidon K30, BASF, NJ), 0.5 g of poly(vinylpyrrolidone) (PVP) (Kollidon K90, BASF, NJ) and 20 mg of TEG crosslinker in 20 ml isopropanol. Coatings were made by adding 100 μl coating solution onto PVC Coverslips (Fisher Scientific, Pittsburgh, Pa.) (n=5). Coatings with same PVP concentrations but without crosslinker were used as controls. After air dried, the sample pieces were illuminated for 20 min in a UV crosslinker (UVP CL-1000, Upland, Calif., 254 nm light, 120,000 μJ/cm$^2$), then rinsed for four hours in deionized water with gentle agitation. The sample pieces were then stained with Congo red dye to determine the presence of PVP. The staining results showed that the coatings with TEG crosslinker were positive while the coatings without crosslinker were negative, indicating TEG crosslinker helped to bond PVP onto the PVC surface.

EXAMPLE 24

Synthesis of HEG Photo-Crosslinker 1.70 g of hexaethylene glycol (Aldrich Chemicals, Milwaukee, Wis.) was dried under vacuum at 50° C. for 2 h and dissolved in 50 ml anhydrous tetrahydrofuran. 3.7 g of 4-(bromomethyl)benzophenone (Aldrich Chemicals, Milwaukee, Wis.) and 1.5 g sodium hydride (60% in mineral oil, Aldrich Chemicals, Milwaukee, Wis.) were added to the solution. The mixture was stirred overnight under refluxing condition and argon protection. The reaction solution was cooled to room temperature and filtered. The filtrate was concentrated by rotary evaporation and the residue was purified on column chromatography (silica gel, 230-400 mesh, Whatman, Inc.) using 25:1 chloroform/methanol mixture as eluent. The fractions containing the pure product were combined and concentrated to dryness by rotary evaporation to yield yellowish oil (yield 70%).

The HEG crosslinker is very soluble in most common solvents including chloroform, methylene chloride, tetrahydrofuran, acetone, ethyl acetate, isopropanol, etc and slightly soluble in water. $^1$H NMR (CDCl$_3$) confirmed the structure of the product. The peaks at 7.26~7.79 ppm (m, 18H) were the typical signals from 4-subsituted benzophenone. The peak at 4.64 ppm (s, 4H) was assigned to the protons of methylene connected to benzophenone group. The peak at 3.66 ppm (m, 24H) corresponded to ethylene groups.

EXAMPLE 25

Coating with HEG Photo-Crosslinker

A coating solution was made by dissolving 0.5 g of poly (vinylpyrrolidone) (PVP) (Kollidon K30, BASF, NJ), 0.5 g of poly(vinylpyrrolidone) (PVP) (Kollidon K90, BASF, NJ) and 20 mg of HEG crosslinker in 20 ml isopropanol. Coatings were made by adding 100 μl coating solution onto PVC Coverslips (Fisher Scientific, Pittsburgh, Pa.) (n=5). Coatings with same PVP concentrations but without crosslinker were used as controls. After air dried, the sample pieces were illuminated for 20 min in a UV crosslinker (UVP CL-1000, Upland, Calif., 254 nm light, 120,000 μJ/cm$^2$), then rinsed for four hours in deionized water with gentle agitation. The sample pieces were then stained with Congo red dye to determine the presence of PVP. The staining results showed that the coatings with HEG crosslinker were positive while the coatings without crosslinker were negative, indicating HEG crosslinker helped to bond PVP onto the PVC surface.

Explanation of + scale for examples 14 through 25. +++ indicates a full coating, no obvious removal of coating from the piece and a bright red color. ++ is slight removal but majority is still intact, color is still red but may be slightly less red or blotchy. + indicates significant removal of coating, but still coating present. The color is typically pink. In most cases the color is simply less as part of the coating is rubbed away fairly uniformly. − indicates no coating remains, no color at all from the stain.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claim.

What is claimed is:

1. A compound of formula:
L-(D-T-C($R^1$)(XP)CHR$^2$GR$^3$C(=O)R$^4$)$_m$
wherein
L is a linking group comprising
a formula according to structure (I):

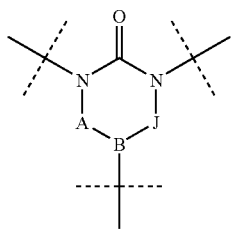

A, B and J form a ring, wherein A and J are C=O;
B is NR$^{11}$;
R$^{11}$ is a hydrogen atom, an alkyl group, an aryl group or denotes a bond with T;
D is CR$^6$R$^7$;
T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;
R$^1$ is a hydrogen atom, an alkyl, alkyloxyalkyl, aryl, aryloxyalkyl or aryloxyaryl group;
X is O, S, or NR$^8$R$^9$;
P is a hydrogen atom or a protecting group, with the proviso that P is absent when X is NR$^8$R$^9$;
R$^2$ is a hydrogen atom, an alkyl, alkyloxyalkyl, aryl, aryloxyalkyl or aryloxyaryl group;
G is —C(=O)O—, —O—, —NHC(=O)O—, —NHC(=O)S—, —SO$_2$—, —CONH—, —NHCONH—, —NHC(=S)NH—, —NR$^{10}$—, —SO$_2$NH—, —C(=N)—, —C(=O)— or —(CH$_2$)$_t$—O—;
R$^3$ and R$^4$ are each independently an alkyl, aryl, arylalkyl, heteroaryl, or an heteroarylalkyl group or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
R$^{10}$ is a hydrogen atom or an alkyl, aryl or arylalkyl group;
R$^6$ and R$^7$ are each independently a hydrogen atom, an alkyl, aryl, arylalkyl, heteroaryl or heteroarylalkyl group;
R$^8$ and R$^9$ are each independently a hydrogen atom, an alkyl, aryl, or arylalkyl group;
R is a hydrogen atom, an alkyl or an aryl group;
q is an integer from 1 to about 7;
r is an integer from 0 to about 3;
s is an integer from 0 to about 3;
m is an integer from 2 to about 10;
t is an integer from 1 to about 10; and
x is an integer from 1 to about 500.

2. A compound of formula:
L-(T-C($R^1$)(XP)CHR$^2$GR$^3$C(=O)R$^4$)$_m$
wherein
L is a linking group comprising
a formula according to structure (I):

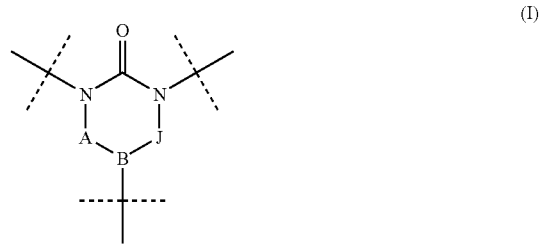

A, B and J form a ring, wherein A and J are C=O;
B is NR$^{11}$;
R$^{11}$ is a hydrogen atom, an alkyl group, an aryl group or denotes a bond with T;
T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;
R$^1$ is a hydrogen atom, an alkyl, alkyloxyalkyl, aryl, aryloxyalkyl or aryloxyaryl group;
X is O, S, or NR$^8$R$^9$;
P is a hydrogen atom or a protecting group, with the proviso that P is absent when X is NR$^8$R$^9$;
R$^2$ is a hydrogen atom, an alkyl, alkyloxyalkyl, aryl, aryloxyalkyl or aryloxyaryl group;
G is, —C(=O)O—, —O—, —NHC(=O)O—, —NHC(=O)S—, —SO$_2$—, —CONH—, —NHCONH—, —NHC(=S)NH—, —NR$^{10}$—, —SO$_2$NH—, —C(=N)—, —C(=O)— or —(CH$_2$)$_t$—O—;
R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
R$^{10}$ is a hydrogen atom or an alkyl, aryl or arylalkyl group;
R$^8$ and R$^9$ are each independently a hydrogen atom, an alkyl, aryl, or arylalkyl group;
R is a hydrogen atom, an alkyl or aryl group;
q is an integer from 1 to about 7;
r is an integer from 0 to about 3;
s is an integer from 0 to about 3;
m is an integer from 2 to about 10;
t is an integer from 1 to about 10; and
x is an integer from 1 to about 500.

3. A compound of formula:
L-(GTZR$^3$C(=O)R$^4$)$_m$
wherein
L is a linking group comprising
a formula according to structure (I):

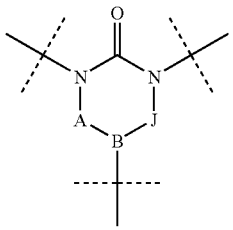

(I)

A, B and J form a ring, wherein A and J are C=O;
B is $NR^{11}$;
$R^{11}$ is a hydrogen atom, an alkyl group, an aryl group or denotes a bond;
T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond;
G is $-C(=O)O-$, $-NHC(=O)O-$, $-NHC(=O)S-$, $-CONH-$, $-NHCONH-$, $-NHC(=S)NH-$, $-C(=N)-$, $-C(=O)-$ or $-(CH_2)_t-O-$;
Z is C=O, COO, or CONH when T is $(-CH_2-)_x$;
$R^3$ and $R^4$ are each independently an alkyl, aryl, arylalkyl, heteroaryl, or an heteroarylalkyl group, or optionally, $R^3$ and $R^4$ can be tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$ or $(-CH_2-)_rS(O)_2(-CH_2-)_s$, $(-CH_2-)_rNR(-CH_2-)_s$;
R is a hydrogen atom or an alkyl or aryl group;
q is an integer from 1 to about 7;
r is an integer from 0 to about 3;
s is an integer from 0 to about 3;
m is an integer from 2 to about 10;
t is an integer from 1 to about 10; and
x is an integer from 1 to about 500.

4. A compound of formula:
$L-(TGQR^3C(=O)R^4)_m$
wherein
L is a linking group comprising
a formula according to structure (I):

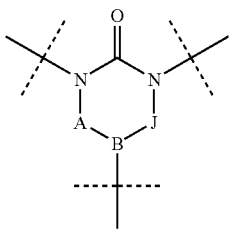

(I)

A, B and J form a ring, wherein A and J are C=O;
B is $NR^{11}$;
$R^{11}$ is a hydrogen atom, an alkyl group, an aryl group or denotes a bond with T;
T is $(-CH_2-)_x$, $(-CH_2CH_2-O-)_x$, $(-CH_2CH_2CH_2-O-)_x$, $(-CH_2CH_2CH_2CH_2-O-)_x$ or forms a bond;
G is $-C(=O)O-$, $-O-$, $-NHC(=O)O-$, $-NHC(=O)S-$, $-SO_2-$, $-CONH-$, $-NHCONH-$, $-NHC(=S)NH-$, $-NR^{10}-$, $-SO_2NH-$, $-C(=N)-$, $-C(=O)-$ or $-(CH_2)_t-O-$;

Q is $(-CH_2-)_p$, $(-CH_2CH_2-O-)_p$, $(-CH_2CH_2CH_2-O-)_p$ or $(-CH_2CH_2CH_2CH_2-O-)_p$;
$R^3$ and $R^4$ are each independently an alkyl, aryl, arylalkyl, heteroaryl, or an heteroarylalkyl group, or optionally, $R^3$ and $R^4$ can be tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$ or $(-CH_2-)_rS(O)_2(-CH_2-)_s$, $(-CH_2-)_rNR(-CH_2-)_s$;
$R^{10}$ is a hydrogen atom or an alkyl, aryl, or an arylalkyl group;
R is a hydrogen atom or an alkyl or aryl group;
q is an integer from 1 to about 7;
r is an integer from 0 to about 3;
s is an integer from 0 to about 3;
m is an integer from 2 to about 10;
p is an integer from 1 to about 10;
t is an integer from 1 to about 10; and
x is an integer from 1 to about 500.

5. A compound of formula:
$L-(-CH_2-)_{xx}C(R^1)(GR^3C(=O)R^4)_m$
wherein
L is a linking group comprising
a formula according to structure (I):

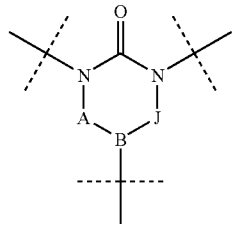

(I)

A, B and J form a ring, wherein A and J are C=O;
B is $NR^{11}$;
$R^{11}$ is a hydrogen atom, an alkyl group, an aryl group or denotes a bond;
$R^1$ is a hydrogen atom, an alkyl, alkyloxyalkyl, aryl, aryloxyalkyl, or aryloxyaryl group;
each G is $-C(=O)O-$, $-O-$, $-NHC(=O)O-$, $-NHC(=O)S-$, $-SO_2-$, $-CONH-$, $-NHCONH-$, $-NHC(=S)NH-$, $-NR^{10}-$, $-SO_2NH-$, $-C(=N)-$, $-C(=O)-$ or $-(CH_2)_t-O-$;
each $R^3$ and $R^4$ are each independently an alkyl, aryl, arylalkyl, heteroaryl, or an heteroarylalkyl group, or optionally, $R^3$ and $R^4$ can be tethered together via $(-CH_2-)_q$, $(-CH_2-)_rC=O(-CH_2-)_s$, $(-CH_2-)_rS(-CH_2-)_s$, $(-CH_2-)_rS=O(-CH_2-)_s$ or $(-CH_2-)_rS(O)_2(-CH_2-)_s$, $(-CH_2-)_rNR(-CH_2-)_s$;
each $R^{10}$ is a hydrogen atom or an alkyl, aryl, or an arylalkyl group;
each R is a hydrogen atom or an alkyl or aryl group;
each q is an integer from 1 to about 7;
each r is an integer from 0 to about 3;
each s is an integer from 0 to about 3;
m is an integer from 2 to about 10;
each t is an integer from 1 to about 10; and
xx is an integer from 1 to about 10.

6. The compound of claim 5, wherein xx is 1, each G is $(-CH_2-)_tO-$ and t is 1, each $R^1$ is H and each $R^3$ and $R^4$ are each individually aryl groups.

7. A compound of formula:
L-(—C(R¹)(XP)CHR²GR³C(=O)R⁴)$_m$
wherein
L is a linking group comprising
a formula according to structure (I):

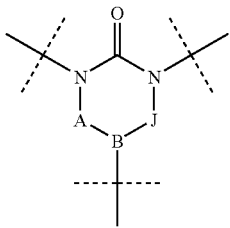

A, B and J form a ring, wherein A and J are C=O;
B is NR¹¹;
R¹¹ is a hydrogen atom, an alkyl group, an aryl group or denotes a bond;
R¹ is a hydrogen atom, an alkyl, alkyloxyalkyl, aryl, aryloxyalkyl or aryloxyaryl group;
X is O, S, or NR⁸R⁹;
P is a hydrogen atom or a protecting group, with the proviso that P is absent when X is NR⁸R⁹;
R² is a hydrogen atom, an alkyl, alkyloxyalkyl, aryl, aryloxyalkyl or aryloxyaryl group;
G is —C(=O)O—, —O—, —NHC(=O)O—, —NHC(=O)S—, —SO₂—, —CONH—, —NHCONH—, —NHC(=S)NH—, —NR¹⁰—, —SO₂NH—, —C(=N)—, —C(=O)— or —(CH₂)$_t$—O—;
R³ and R⁴ are each independently an alkyl, aryl, arylalkyl, heteroaryl, or an heteroarylalkyl group, or optionally, R³ and R⁴ can be tethered together via (—CH₂—)$_q$, (—CH₂—)$_r$C=O(—CH₂—)$_s$, (—CH₂—)$_r$S(—CH₂—)$_s$, (—CH₂—)$_r$S=O(—CH₂—)$_s$ or (—CH₂—)$_r$S(O)₂(—CH₂—)$_s$, (—CH₂—)$_r$NR(—CH₂—)$_s$;
R⁸ and R⁹ are each independently a hydrogen atom, an alkyl, aryl, or arylalkyl group;
R¹⁰ is a hydrogen atom or an alkyl, aryl, or an arylalkyl group;
R is a hydrogen atom, an alkyl or an aryl group;
q is an integer from 1 to about 7;
r is an integer from 0 to about 3;
s is an integer from 0 to about 3;
m is an integer from 2 to about 10; and
t is an integer from 1 to about 10.

8. A compound of formula:
L-(GR³C(=O)R⁴)$_m$;
wherein
L is a linking group comprising
a formula according to structure (I):

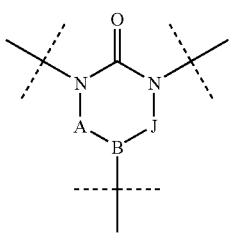

A, B and J form a ring, wherein A and J are C=O;
B is NR¹¹;
R¹¹ is a hydrogen atom, an alkyl group, an aryl group or denotes a bond;
G is —C(=O)O—, —NHC(=O)O—, —NHC(=O)S—, —CONH—, —NHCONH—, —NHC(=S)NH—, —C(=N)—, —C(=O)— or —(CH₂)$_t$—O—;
R³ and R⁴ are each independently an alkyl, aryl, arylalkyl, heteroaryl, or an heteroarylalkyl group, or optionally, R³ and R⁴ can be tethered together via (—CH₂—)$_q$, (—CH₂—)$_r$C=O(—CH₂—)$_s$, (—CH₂—)$_r$S(—CH₂—)$_s$, (—CH₂—)$_r$S=O(—CH₂—)$_s$ or (—CH₂—)$_r$S(O)₂(—CH₂—)$_s$, (—CH₂—)$_r$NR(—CH₂—)$_s$;
R is a hydrogen atom, an alkyl or an aryl group;
q is an integer from 1 to about 7;
r is an integer from 0 to about 3;
s is an integer from 0 to about 3;
m is an integer from 2 to about 10; and
t is an integer from 1 to about 10.

9. A method to modify a substrate comprising the step of applying a compound of formula:
L-(D-T-C(R¹)(XP)CHR²GR³C(=O)R⁴)$_m$
wherein
L is a linking group comprising
a formula according to structure (I):

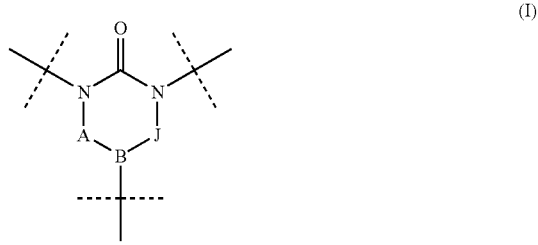

A, B and J form a ring, wherein A and J are C=O;
B is NR¹¹;
R¹¹ is a hydrogen atom, an alkyl group, an aryl group or denotes a bond;
D is CR⁶R⁷;
T is (—CH₂—)$_x$, (—CH₂CH₂—O—)$_x$, (—CH₂CH₂CH₂—O—)$_x$, (—CH₂CH₂CH₂CH₂—O—)$_x$ or forms a bond;
R¹ is a hydrogen atom, an alkyl, alkyloxyalkyl, aryl, aryloxyalkyl or aryloxyaryl group;
X is O, S, or NR⁸R⁹;
P is a hydrogen atom or a protecting group, with the proviso that P is absent when X is NR⁸R⁹;
R² is a hydrogen atom, an alkyl, alkyloxyalkyl, aryl, aryloxyalkyl or aryloxyaryl group;
G is —C(=O)O—, —O—, —NHC(=O) O—, —NHC(=O)S—, —SO₂—, —CONH—, —NHCONH—, —NHC(=S)NH—, —NR¹⁰—, —SO₂NH—, —C(=N)—, —C(=O)— or —(CH₂)$_t$—O—;
R³ and R⁴ are each independently an alkyl, aryl, arylalkyl, heteroaryl, or an heteroarylalkyl group or optionally, R³ and R⁴ can be tethered together via (—CH₂—)$_q$, (—CH₂—)$_r$C=O(—CH₂—)$_s$, (—CH₂—)$_r$S(—CH₂—)$_s$, (—CH₂—)$_r$S=O(—CH₂—)$_s$ or (—CH₂—)$_r$S(O)₂(—CH₂—)$_s$, (—CH₂—)$_r$NR(—C-H₂—)$_s$;
R¹⁰ is a hydrogen atom or an alkyl, aryl or arylalkyl group;
R⁶ and R⁷ are each independently a hydrogen atom, an alkyl, aryl, arylalkyl, heteroaryl or heteroarylalkyl group;

$R^8$ and $R^9$ are each independently a hydrogen atom, an alkyl, aryl, or arylalkyl group;

R is a hydrogen atom, an alkyl or an aryl group;

q is an integer from 1 to about 7;

r is an integer from 0 to about 3;

s is an integer from 0 to about 3;

m is an integer from 2 to about 10;

t is an integer from 1 to about 10; and x is an integer from 1 to about 500 to the surface of the substrate, such that the substrate surface is modified.

10. The method of claim 9, wherein the compound is photoactivated such that at least one photoactivatable group within the compound forms a bond with the surface of the substrate.

11. A method to modify a substrate comprising the step of applying a compound of formula:

L-(T-C($R^1$)(XP)CH$R^2$G$R^3$C(=O)$R^4$)$_m$ wherein

L is a linking group comprising a formula according to structure (I):

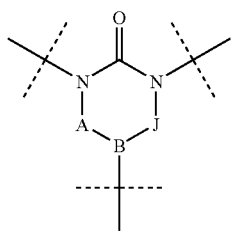

(I)

A, B and J form a ring, wherein A and J are C=O;

B is $NR^{11}$;

$R^{11}$ is a hydrogen atom, an alkyl group, an aryl group or denotes a bond with T;

T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;

$R^1$ is a hydrogen atom, an alkyl, alkyloxyalkyl, aryl, aryloxyalkyl or aryloxyaryl group;

X is O, S, or $NR^8R^9$;

P is a hydrogen atom or a protecting group, with the proviso that P is absent when X is $NR^8R^9$;

$R^2$ is a hydrogen atom, an alkyl, alkyloxyalkyl, aryl, aryloxyalkyl or aryloxyaryl group;

G is —C(=O)O—, —O—, —NHC(=O)O—, —NHC(=O)S—, —CONH—, —NHCONH—, —NHC(=S)NH—, —$NR^{10}$—, —SO$_2$NH—, —C(=N)—, —C(=O)— or —(CH$_2$)$_t$—O—;

$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

$R^{10}$ is a hydrogen atom or an alkyl, aryl or arylalkyl group;

$R^8$ and $R^9$ are each independently a hydrogen atom, an alkyl, aryl, or arylalkyl group;

R is a hydrogen atom, an alkyl or aryl group;

q is an integer from 1 to about 7;

r is an integer from 0 to about 3;

s is an integer from 0 to about 3;

m is an integer from 2 to about 10;

t is an integer from 1 to about 10; and x is an integer from 1 to about 500 to the surface of the substrate, such that the substrate surface is modified.

12. The method of claim 11, wherein the compound is photoactivated such that at least one photoactivatable group within the compound forms a bond with the surface of the substrate.

13. A method to modify a substrate comprising the step of applying a compound of formula:

L-(GTZ$R^3$C(=O)$R^4$)$_m$ wherein

L is a linking group comprising a formula according to structure (I):

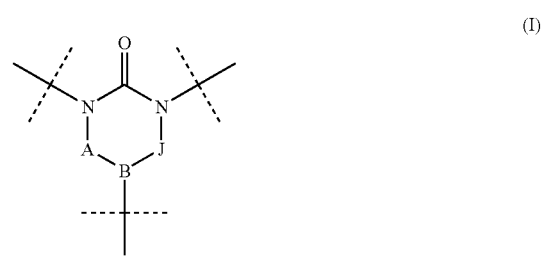

(I)

A, B and J form a ring, wherein A and J are C=;

B is $NR^{11}$;

$R^{11}$ is a hydrogen atom, an alkyl group, an aryl group or denotes a bond;

T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;

G is —C(=O) O—, —NHC(=O) O—, —NHC(=O) S—, —CONH—, —NHCONH—, —NHC(=S)NH—, —C(=N)—, —C(=O)— or —(CH$_2$)$_t$—O—;

Z is C=O, COO, or CONH when T is (—CH$_2$—)$_x$;

$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;

R is a hydrogen atom or an alkyl or aryl group;

q is an integer from 1 to about 7;

r is an integer from 0 to about 3;

s is an integer from 0 to about 3;

m is an integer from 2 to about 10;

t is an integer from 1 to about 10; and x is an integer from 1 to about 500 to the surface of the substrate, such that the substrate surface is modified.

14. The method of claim 13, wherein the compound is photoactivated such that at least one photoactivatable group within the compound forms a bond with the surface of the substrate.

15. A method to modify a substrate comprising the step of applying a compound of formula:

L-(TGQ$R^3$C(=O)$R^4$)$_m$ wherein

L is a linking group comprising a formula according to structure (I):

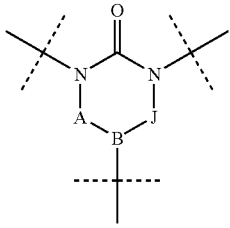

A, B and J form a ring, wherein A and J are C═O;
B is NR$^{11}$;
R$^{11}$ is a hydrogen atom, an alkyl group, an aryl group or denotes a bond with T;
T is (—CH$_2$—)$_x$, (—CH$_2$CH$_2$—O—)$_x$, (—CH$_2$CH$_2$CH$_2$—O—)$_x$, (—CH$_2$CH$_2$CH$_2$CH$_2$—O—)$_x$ or forms a bond;
G is, —C(═O) O—, —O—, —NHC(═O)O—, —NHC(═O)S—, —SO$_2$—, —CONH—, —NHCONH—, —NHC(═S)NH—, —NR$^{10}$—, —SO$_2$NH—, —C(═N)—, —C(═O)— or —(CH$_2$)$_t$—O—;
Q is (—CH$_2$—)$_p$, (—CH$_2$CH$_2$—O—)$_p$, (—CH$_2$CH$_2$CH$_2$—O—)$_p$ or (—CH$_2$CH$_2$CH$_2$CH$_2$—O—)$_p$;
R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C═O(—CH$_2$—)$_s$, (—CH$_2$—)$_r$S(—CH$_2$—)$_s$, (—CH$_2$—)$_r$S═O(—CH$_2$—)$_s$ or (—CH$_2$—)$_r$S(O)$_2$(—CH$_2$—)$_s$, (—CH$_2$13)$_r$NR(—CH$_2$—)$_s$;
R$^{10}$ is a hydrogen atom or an alkyl, aryl, or an arylalkyl group;
R is a hydrogen atom or an alkyl or aryl group;
q is an integer from 1 to about 7;
r is an integer from 0 to about 3;
s is an integer from 0 to about 3;
m is an integer from 2 to about 10;
p is an integer from 1 to about 10;
t is an integer from 1 to about 10; and
x is an integer from 1 to about 500 to the surface of the substrate, such that the substrate surface is modified.

16. The method of claim 15, wherein the compound is photoactivated such that at least one photoactivatable group within the compound forms a bond with the surface of the substrate.

17. A method to modify a substrate comprising the step of applying a compound of formula:
L-(—CH$_2$—)$_{xx}$C(R$^1$)(GR$^3$C(═O)R$^4$)$_m$
wherein
L is a linking group comprising

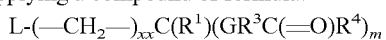

a formula according to structure (I):

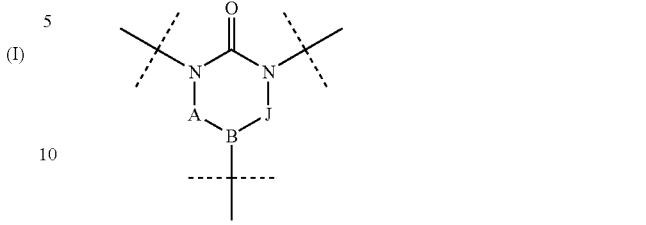

A, B and J form a ring, wherein A and J are C═O;
B is NR$^{11}$;
R$^{11}$ is a hydrogen atom, an alkyl group, an aryl group or denotes a bond;
R$^1$ is a hydrogen atom, an alkyl, alkyloxyalkyl, aryl, aryloxyalkyl, or aryloxyaryl group;
each G is —C(═O) O—, —O—, —NHC(═O)O—, —NHC(═O)S—, —SO$_2$—, —CONH—, —NH-CONH—, —NHC(═S)NH—, —NR$^{10}$—, —SO$_2$NH—, —C(═N)—, —C(═O)— or —(CH$_2$)$_t$—O—;
each R$^3$ and R$^4$ are each independently an alkyl, aryl, arylalkyl, heteroaryl, or an heteroarylalkyl group, or optionally, R$^3$ and R$^4$ can be tethered together via (—CH$_2$—)$_q$, (—CH$_2$—)$_r$C═O(—CH$_2$—)$_s$, (—CH$_2$—)$_r$S(—CH$_2$—)$_s$, (—CH$_2$—)$_r$S═O(—CH$_2$—)$_s$ or (—CH$_2$—)$_r$S(O)$_2$(—CH$_2$—)$_s$, (—CH$_2$—)$_r$NR(—CH$_2$—)$_s$;
each R$^{10}$ is a hydrogen atom or an alkyl, aryl, or an arylalkyl group;
each R is a hydrogen atom or an alkyl or aryl group;
each q is an integer from 1 to about 7;
each r is an integer from 0 to about 3;
each s is an integer from 0 to about 3;
m is an integer from 2 to about 10;
each t is an integer from 1 to about 10; and
xx is an integer from 1 to about 10 to the surface of the substrate, such that the substrate surface is modified.

18. The method of claim 17, wherein the compound is photoactivated such that at least one photoactivatable group within the compound forms a bond with the surface of the substrate.

19. A method to modify a substrate comprising the step of applying a compound of formula:
L-(—C(R$^1$)(XP)CHR$^2$GR$^3$C(═O)R$^4$)$_m$
wherein
L is a linking group comprising
a formula according to structure (I):

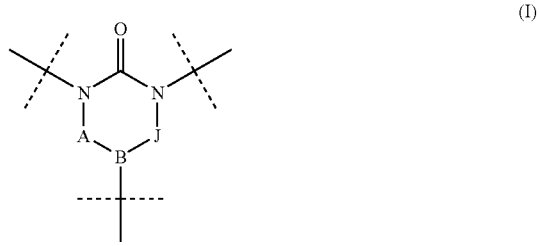

A, B and J form a ring, wherein A and J are C=O;
B is $NR^{11}$;
$R^{11}$ is a hydrogen atom, an alkyl group, an aryl group or denotes a bond;
$R^1$ is a hydrogen atom, an alkyl, alkyloxyalkyl, aryl, aryloxyalkyl or aryloxyaryl group;
X is O, S, or $NR^8R^9$;
P is a hydrogen atom or a protecting group, with the proviso that P is absent when X is $NR^8R^9$;
$R^2$ is a hydrogen atom, an alkyl, alkyloxyalkyl, aryl, aryloxyalkyl or aryloxyaryl group;
G is —C(=O)O—, —O—, —NHC(=O)O—, —NHC(=O)S—, —SO$_2$—, —CONH—, —NHCONH—, —NHC(=S)NH—, —NR$^{10}$—, —SO$_2$NH—, —C(=N)—, —C(=O)— or —(CH$_2$)$_t$—O—;
$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
$R^8$ and $R^9$ are each independently a hydrogen atom, an alkyl, aryl, or arylalkyl group;
$R^{10}$ is a hydrogen atom or an alkyl, aryl, or an arylalkyl group;
R is a hydrogen atom, an alkyl or an aryl group;
q is an integer from 1 to about 7;
r is an integer from 0 to about 3;
s is an integer from 0 to about 3;
m is an integer from 2 to about 10; and
t is an integer from 1 to about 10 to the surface of the substrate, such that the substrate surface is modified.

20. The method of claim 19, wherein the compound is photoactivated such that at least one photoactivatable group within the compound forms a bond with the surface of the substrate.

21. A method to modify a substrate comprising the step of applying a compound of formula:
L-(GR$^3$C(=O)R$^4$)$_m$;
wherein
L is a linking group comprising a formula according to structure (I):

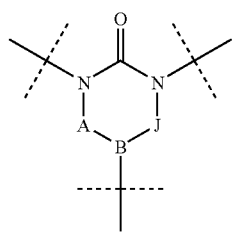

(I)

A, B and J form a ring, wherein A and J are C=O;
B is $NR^{11}$;
$R^{11}$ is a hydrogen atom, an alkyl group, an aryl group or denotes a bond;
G is —C(=O)O—, —NHC(=O)O—, —NHC(=O)S—, —CONH—, —NHCONH—, —NHC(=S)NH—, —C(=N)—, —C(=O)— or —(CH$_2$)$_t$—O—;
$R^3$ and $R^4$ are each independently an alkyl, aryl, arylalkyl, heteroaryl, or an heteroarylalkyl group, or optionally, $R^3$ and $R^4$ can be tethered together via (—CH$_2$—)$_q$, (—CH$_2$—)$_r$C=O(—CH$_2$—)$_s$, (—CH$_2$—)$_r$S(—CH$_2$—)$_s$, (—CH$_2$—)$_r$S=O(—CH$_2$—)$_s$ or (—CH$_2$—)$_r$S(O)$_2$(—CH$_2$—)$_s$, (—CH$_2$—)$_r$NR(—CH$_2$—)$_s$;
R is a hydrogen atom, an alkyl or an aryl group;
q is an integer from 1 to about 7;
r is an integer from 0 to about 3;
s is an integer from 0 to about 3;
m is an integer from 2 to about 10; and
t is an integer from 1 to about 10 to the surface of the substrate, such that the substrate surface is modified.

22. The method of claim 21, wherein the compound is photoactivated such that at least one photoactivatable group within the compound forms a bond with the surface of the substrate.

23. The method of claim 22, wherein the compound is photoactivated such that at least one photoactivatable group within the compound forms a bond with the surface of the substrate.

* * * * *

UNITED STATES PATENT AND TRADEMARK OFFICE
CERTIFICATE OF CORRECTION

| | | |
|---|---|---|
| PATENT NO. | : 7,772,393 B2 | Page 1 of 1 |
| APPLICATION NO. | : 11/423503 | |
| DATED | : August 10, 2010 | |
| INVENTOR(S) | : Patrick Guire, Kristin Taton and Jie Wen | |

It is certified that error appears in the above-identified patent and that said Letters Patent is hereby corrected as shown below:

Insert — Column 1, line 3 -- This invention was made with government support under 7R44HL066933-03 awarded by the National Institutes of Health. The government has certain rights in the invention. --

Signed and Sealed this
Twenty-second Day of February, 2011

David J. Kappos
*Director of the United States Patent and Trademark Office*